(12) United States Patent
Miller et al.

(10) Patent No.: US 9,859,594 B2
(45) Date of Patent: Jan. 2, 2018

(54) ASSET MANAGEMENT FOR PHYSICAL ASSETS

(71) Applicant: Enovate Medical, LLC, Murfreesboro, TN (US)

(72) Inventors: David R. Miller, Murfreesboro, TN (US); Allen Kilbourne, Canton, MI (US); Mary Metelko, Murfreesboro, TN (US)

(73) Assignee: Enovate Medical, LLC, Murfreesboro, TN (US)

( * ) Notice: Subject to any disclaimer, the term of this patent is extended or adjusted under 35 U.S.C. 154(b) by 596 days.

(21) Appl. No.: 14/323,325

(22) Filed: Jul. 3, 2014

(65) Prior Publication Data

US 2015/0362333 A1   Dec. 17, 2015

Related U.S. Application Data

(60) Provisional application No. 62/010,921, filed on Jun. 11, 2014.

(51) Int. Cl.
| | |
|---|---|
| *H01M 10/659* | (2014.01) |
| *H02J 5/00* | (2016.01) |
| *H02J 7/02* | (2016.01) |
| *H01M 10/658* | (2014.01) |
| *H01M 2/10* | (2006.01) |

(Continued)

(52) U.S. Cl.
CPC ....... *H01M 10/659* (2015.04); *H01M 2/1022* (2013.01); *H01M 2/1264* (2013.01); *H01M 2/348* (2013.01); *H01M 10/46* (2013.01); *H01M 10/482* (2013.01); *H01M 10/486* (2013.01); *H01M 10/658* (2015.04); *H02J 5/005* (2013.01); *H02J 7/007* (2013.01); *H02J 7/0021* (2013.01); *H02J 7/0044* (2013.01); *H02J 7/0047* (2013.01); *H02J 7/025* (2013.01); *H02J 17/00* (2013.01); *H02J 50/10* (2016.02); *H02J 50/40* (2016.02); *H02J 50/50* (2016.02); *H02J 50/80* (2016.02); *H04B 5/0037* (2013.01); *H04Q 9/00* (2013.01); *G01V 3/12* (2013.01); *H01M 2200/10* (2013.01); *H01M 2200/103* (2013.01); *H01M 2220/30* (2013.01); *H04B 5/0081* (2013.01); *Y10T 307/469* (2015.04)

(58) Field of Classification Search
None
See application file for complete search history.

(56) References Cited

U.S. PATENT DOCUMENTS

| | | | | |
|---|---|---|---|---|
| 8,663,106 B2* | 3/2014 | Stivoric | ............ | G06F 19/3418 374/164 |
| 2012/0249051 A1* | 10/2012 | Son | ........ | H02J 7/025 320/106 |

(Continued)

*Primary Examiner* — John A Tweel, Jr.
*Assistant Examiner* — Jerold Murphy
(74) *Attorney, Agent, or Firm* — Waller Lansden Dortch & Davis, LLP; Nathan J. Bailey; Mark A. Pitchford

(57) ABSTRACT

A technology is discussed for a wireless transfer station that is operable to communicate management information. Measurement information can be received from one or more other wireless transfer stations. The measurement information can be aggregated from the one or more other wireless transfer stations. The measurement information can be analyzed to determine a status of the one or more wireless transfer stations using the aggregated energy measurement information.

4 Claims, 29 Drawing Sheets

(51) Int. Cl.

| | | |
|---|---|---|
| *H01M 2/12* | (2006.01) | |
| *H01M 2/34* | (2006.01) | |
| *H01M 10/48* | (2006.01) | |
| *H02J 7/00* | (2006.01) | |
| *H04B 5/00* | (2006.01) | |
| *H02J 17/00* | (2006.01) | |
| *H04Q 9/00* | (2006.01) | |
| *H01M 10/46* | (2006.01) | |
| *H02J 50/10* | (2016.01) | |
| *H02J 50/40* | (2016.01) | |
| *H02J 50/80* | (2016.01) | |
| *H02J 50/50* | (2016.01) | |
| *G01V 3/12* | (2006.01) | |

(56) References Cited

U.S. PATENT DOCUMENTS

| | | | | |
|---|---|---|---|---|
| 2012/0265355 A1* | 10/2012 | Bernheim | ............... | G05B 15/02 |
| | | | | 700/286 |
| 2013/0026981 A1* | 1/2013 | Van Der Lee | .......... | H02J 5/005 |
| | | | | 320/108 |
| 2013/0200721 A1* | 8/2013 | Kurs | ................... | H04B 5/0037 |
| | | | | 307/104 |
| 2013/0241474 A1* | 9/2013 | Moshfeghi | ............ | H02J 7/0027 |
| | | | | 320/108 |
| 2014/0002014 A1* | 1/2014 | Sultenfuss | .............. | H02J 7/025 |
| | | | | 320/108 |
| 2014/0191568 A1* | 7/2014 | Partovi | .................. | H02J 7/025 |
| | | | | 307/9.1 |

\* cited by examiner

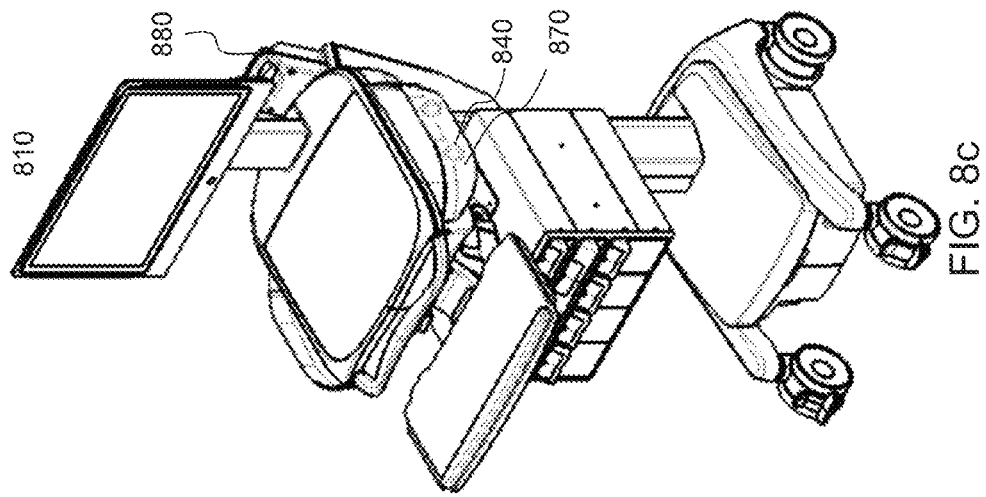
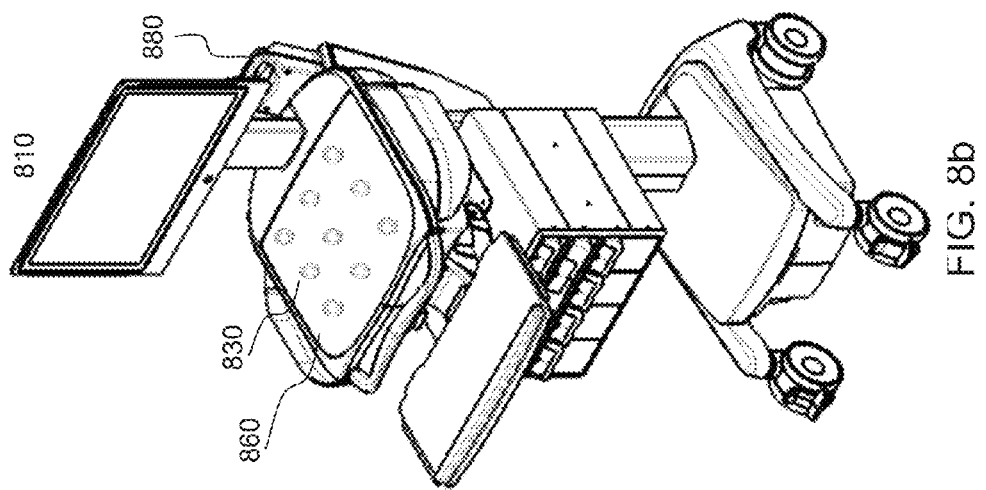
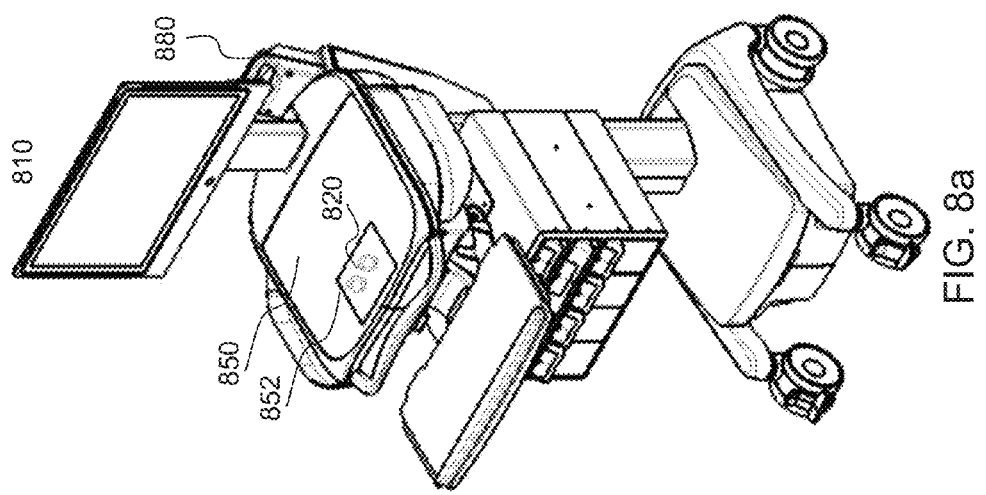

ASSET MANAGEMENT FOR PHYSICAL ASSETS

This application claims the benefit of and hereby incorporates by reference U.S. Provisional Patent Application Ser. No. 62/010,921, filed Jun. 11, 2014.

BACKGROUND

Medical facilities, such as hospitals, health care centers, and nursing homes, can invest heavily in physical assets, such as gurneys, medical carts, diagnostic equipment, monitoring equipment, treatment equipment, bandages and other supplies, drugs, and so forth in order to provide medical treatment to patients. Hospitals must purchase and maintain physical assets to perform testing procedures, perform scans, determine medical diagnoses of patients, and perform advanced surgical procedures. Many of the assets at a medical facility are mobile or portable. While in some cases, all or part of an asset is disposable and may not be reused, in other cases, assets may be reusable.

Often, hospital equipment can be very costly, and, therefore, the high equipment cost may require that the hospital permit one or more units or floors to share equipment. For example, an ultrasound unit may be capable of being used on one or more floors or hospital units (e.g. gynecology and radiology). Equipment in some instances may be taken from one location in a medical facility to another. Often, equipment remains at the location of the facility at which it was last used. For example, when a patient is transported in a wheelchair by an attendant from a patient's room to a fitness center of a hospital to receive therapy, the wheelchair may be left at the fitness center location. In this example, the patient may be returned to the patient's room by another attendant, who obtained a wheelchair from another location, leaving the original wheelchair at the fitness center. Another example is that a patient may be discharged from a hospital using one of several exit locations of the hospital. If the patient is discharged using a wheelchair, that wheelchair is likely to remain at one of the discharge exit locations.

Tracking the physical assets of a medical facility can be difficult. Radio frequency identification (RFID) tags can be used to determine locations of equipment, supplies, and other physical assets. However, RFID tags have a limited short distance use and, therefore, commonly require RFID tag readers to determine a location of the RFID tags. Additionally, RFID tags used for asset management systems provide a minimal amount of information, such as a location of an object.

Where the physical assets of the medical facility can be expensive and may be used in critical situations, many of the physical assets require regular maintenance and/or replacement. Maintaining a large number of physical assets in a large environment, such as a medical facility can be difficult.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 8a depicts a wheeled medical cart with a plurality of wireless transfer stations integrated into a selected area of a work surface of the wheeled medical cart in accordance with an example;

FIG. 8b depicts a wheeled medical cart with a plurality of wireless transfer stations integrated into a work surface of the wheeled medical cart in accordance with an example;

FIG. 8c depicts a wheeled medical cart with one or more wireless transfer stations integrated into a device holder of the wheeled medical cart in accordance with an example;

Figure 1:
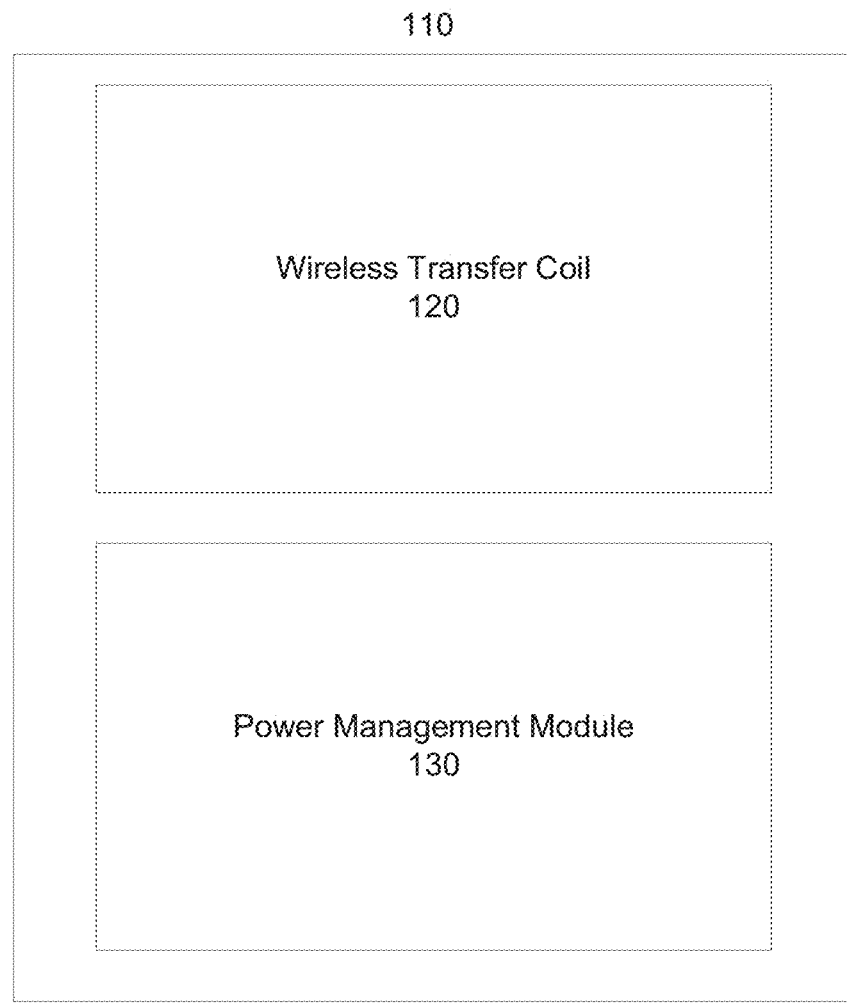
FIG. 1 depicts a wireless transfer station in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

The terms battery, cell, and/or battery cell as used herein can be used interchangeably and can refer to any of a variety of different cell chemistries and configurations. In one embodiment the cell chemistries and configurations can include, but are not limited to, lithium ion (e.g., lithium iron phosphate, lithium cobalt oxide, other lithium metal oxides, etc.), lithium ion polymer, nickel metal hydride, nickel cadmium, nickel hydrogen, nickel zinc, silver zinc, or other battery type/configurations.

The term battery pack as used herein can refer to one or more individual batteries contained within a single piece housing, or a multiple piece housing. The one or more individual batteries can be electrically interconnected in parallel and/or in series to achieve a selected energy level (such as a voltage level or a current level) and capacity level.

Medical facilities can use physical assets including gurneys, medical carts, diagnostic equipment, monitoring equipment, and treatment equipment to provide medical care for patients. Many of the physical assets of the medical facility require energy to function. In one embodiment, the physical assets can receive the energy from a mobile energy source, such as a battery. In another embodiment, the battery can be a rechargeable battery. In one example, the rechargeable battery can be a lead-based battery, a lithium-based battery, a nickel based battery, and so forth. In one embodiment, the rechargeable battery can be recharged using physical electrical contacts. In another embodiment, the rechargeable battery can be recharged via a wireless energy transfer. A wireless energy transfer or wireless energy can be a transmission of electrical energy from an energy source to an electrical load without interconnecting wires or physical electrical contacts.

In one embodiment, a wireless transfer station can provide energy to a physical asset. In another embodiment, a wireless transfer station can be integrated into an electronic device. In another embodiment, the wireless transfer station can be a wireless energy battery pack that can be coupled to another wireless transfer station, such as a wireless transfer station integrated into an electronic device to provide energy to the electronic device. In another embodiment, the wireless transfer station can be integrated into a device, medical equipment, a medical cart, furniture, or other objects. In another embodiment, the wireless transfer station can be a plate or platform that receives energy from an alternative current (AC) outlet and transfers wireless energy to another object, such as another wireless transfer station. In one embodiment, the wireless transfer station can be integrated into a stationary object, such as a floor mat, a plate mounted on a wall, floor tiles, a piece of furniture, and so forth. In another embodiment, the wireless transfer station can be integrated into a portable or mobile object, such as a wheeled medical cart, a medical device, and so forth.

Often, rechargeable batteries are used as a replenishable energy source for electronic devices. In one embodiment, a battery pack can include one or more rechargeable batteries. In one example, the one or more rechargeable batteries can be a lead-based battery, a lithium-based battery, a nickel based battery, or another type of chemical storage battery. Traditionally, a rechargeable battery pack provides energy to an electronic device using physical electrically conductive connections between the rechargeable battery pack and the electronic device. When the traditional rechargeable batteries of the rechargeable battery pack are depleted, the rechargeable batteries can be replenished by connecting physical electrically conductive contacts between the rechargeable battery pack and a battery charger.

In one embodiment of the present invention, a wireless transfer station can receive energy and/or send energy to another device, such as another wireless transfer station, using a wireless energy transfer scheme (e.g. transfer energy without wires). A wireless energy transfer scheme can be any form of wireless energy transfer associated with the use of electric fields, magnetic fields, electromagnetic fields, and so forth that allows electrical energy to be transmitted between two or more wireless transfer elements without using physical electrical contacts. In one example, a wireless energy transfer of wireless energy can be a transfer of electrical energy from an energy source to an electrical load without the use of interconnecting wires or physical electrical contacts.

In one embodiment, the wireless transfer station can include one or more wireless transfer coils to transfer energy and/or data with other wireless transfer stations. The wireless transfer coil can include one or more power management modules to control the energy transfers and/or data transfers with the other wireless transfer stations.

Examples of a wireless transfer station includes a wireless energy rechargeable battery pack, a wireless energy transfer platform and/or data transceiver integrated into a medical cart, a wireless energy transfer platform and/or data transceiver integrated into an electronic device, a wireless energy transfer platform and/or data transceiver integrated into a piece of furniture, a wireless energy transfer platform and/or data transceiver integrated into a plate mounted to a wall, a wireless energy transfer platform and/or data transceiver integrated into a device (such as a medical device or medical equipment), and so forth.

In one example, the wireless transfer station can be a wireless energy battery pack that can be attached to a device, such as a medical cart or medical equipment. The wireless transfer station that transfers energy and/or data with the device can also relay the energy and/or data with other devices and/or wireless transfer stations. These examples are not intended to be limiting. The wireless transfer station can be implemented in a variety of electronic devices and mounting locations.

In one embodiment, the wireless transfer station can receive data from and/or send data or information to another device, such as another wireless transfer station, using a wireless data transfer scheme. In another embodiment, the wireless data transfer scheme can be any form of data transfer associated with a communications network. In another embodiment, the communications network can be a cellular network. The cellular network can be configured to operate based on a cellular standard, such as the third generation partnership projection (3GPP) long term evolution (LTE) Rel. 8, 9, 10, 11, or 12 standard, or the institute of electronic and electrical engineers (IEEE) 802.16p, 802.16n, 802.16m-2011, 802.16h-2010, 802.16j-2009, or 802.16-2009 standard.

In another embodiment, the communications network can be a wireless local area network (such as a wireless fidelity network (Wi-Fi)) that can be configured to operate using a standard such as the IEEE 802.11-2012, IEEE 802.11ac, or IEEE 802.11ad standard. In another embodiment, the communications network can be configured to operate using a Bluetooth standard such as Bluetooth v1.0, Bluetooth v2.0, Bluetooth v3.0, or Bluetooth v4.0. In another embodiment, the communications network can be configured to operate using a ZigBee standard, such as the IEEE 802.15.4-2003 (ZigBee 2003), IEEE 802.15.4-2006 (ZigBee 2006), or IEEE 802.15.4-2007 (ZigBee Pro) standard. In another embodiment, the wireless data transfer scheme can be any form of data transfer associated with electric fields, magnetic fields, or electromagnetic fields that is transmitted between two or more wireless transfer elements without using physical electrical contacts.

In one embodiment, the wireless transfer station can include one or more wireless transfer elements. In one example, a wireless transfer element can be a wireless transfer coil. In one embodiment, the wireless transfer coil can be a coil used for transmitting and/or receiving energy and/or data using magnetic inductance and/or magnetic resonance.

FIG. 1 illustrates a wireless transfer station 110. FIG. 1 further illustrates that the wireless transfer station 110 can include a wireless transfer coil 120 and a power management module 130. In one example, the power management module 130 can convert energy received from an energy source, such as another wireless transfer station or an alternating current (AC) energy outlet, a selected current level, a selected voltage level, and/or a selected wattage level. In another embodiment, the wireless transfer station 110 can include one or more batteries, such as rechargeable batteries. In one embodiment, the wireless transfer coil 120 can comprise a transmitting coil and/or a receiving coil.

Figure 2:
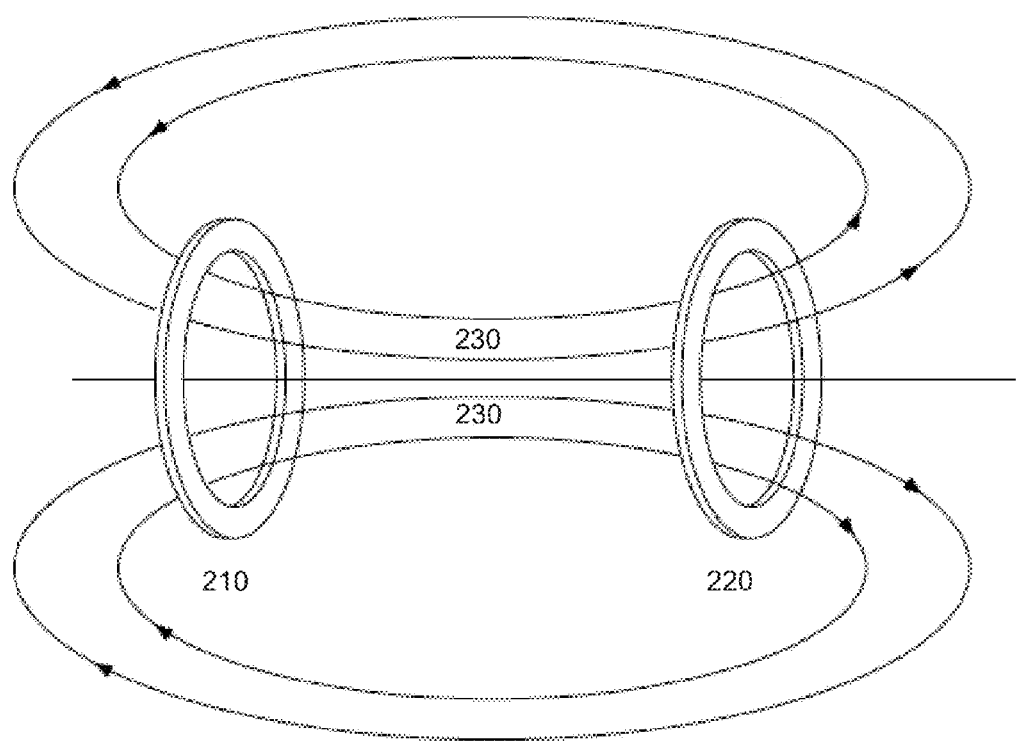
FIG. 2 depicts transferring energy or data between a plurality of wireless transfer coils in accordance with an example.

FIG. 2 illustrates an example of transferring energy or data between a plurality of wireless transfer coils 210 and 220. FIG. 2 further illustrates that one of the plurality of wireless transfer coils 210 can be a transmitting coil 210 and another one of the plurality of wireless transfer coils 220 can be a receiving coil 220. In one embodiment, energy and/or data can be transferred from the transmitting coil 210 to the receiving coil 220 by coupling the transmitting coil 210 with the receiving coil 220 to enable the energy or data to be transferred over a gap or distance. In one example, wireless energy can be transferred by generating a magnetic field 230 (such as an electromagnetic field) at the transmitting coil 210 and positioning the receiving coil 220 within the magnetic field 230 to induce a current at the receiving coil 220. The process of inducing a current at the receiving coil is referred to as coupling the receiving coil 220 to the transmitting coil 210. In one embodiment, the wireless transfer coil coupling for wireless energy or data transfer can be a magnetic induction coupling. In another embodiment, the wireless transfer coil coupling for wireless energy transfer can be a magnetic resonant coupling.

In one embodiment, the transmitting coil 210 can be a transmitting induction coil and the receiving coil 220 can be a receiving induction coil. The wireless transfer station can use a magnetic field to transfer energy between the transmitting coil 210 coupled to a first object (such as a wireless transfer station) and a receiving coil 220 of a second object (such as another wireless transfer station) without any direct contact between the transmitting coil 210 and the receiving coil 220, e.g. inductive coupling.

In one embodiment, inductive coupling can occur when the transmitting coil 210 creates a magnetic field 230 (such as an alternating electromagnetic field) using an energy source, such as an alternating current (AC) energy outlet or a direct current (DC) battery. A current can be induced at the receiving coil 220 using the magnetic field when the receiving coil 220 is located within the magnetic field 230.

In one example, when the transmitting coil 210 and the receiving coil 220 are within a threshold proximity distance, the transmitting coil 210 and the receiving coil 220 can couple to form an electric transformer. In one embodiment, current from the receiving coil 220 can be transferred to a battery or an electronic device. In another embodiment, the current can be stored in one or more energy sources of the wireless transfer station, such as a battery. In another embodiment, the current can be transferred to a device coupled to the wireless transfer station. In one embodiment, an impedance of one or more transmitting coils 210 can be substantially matched with an impedance of one or more receiving coils 220.

In one embodiment, the transmitting coil 210 can be a transmitting resonant coil and the receiving coil 220 can be a receiving resonant coil. A wireless resonant transfer can be a resonant transmission of energy or data between at least one transmitting coil 210 and at least one receiving coil 220. In another embodiment, at least one transmitting coil 210 and at least one receiving coil 220 can be tuned to resonate at a same frequency or a substantially same frequency.

In one example, resonant transmission of wireless energy can occur when the transmitting coil and the receiving coil are constructed to resonate at the same frequency or approximately the same frequency. The transmitting coil 210 can be configured to oscillate current at the resonant frequency of the coils to transfer energy and/or data. The oscillating current of the transmitting coil 210 can generate an oscillating magnetic field at the selected resonant frequency of the receiving coil. When the receiving coil 220 is positioned adjacent to the oscillating magnetic field and constructed to operate at the same frequency or substantially the same frequency as the transmitting coil 210, the receiving coil 220 can receive energy and/or data from the oscillating magnetic field.

In another embodiment, an impedance of one or more transmitting coils 210 can be substantially matched with an impedance of one or more receiving coils 220 for energy and/or data transfer. In another embodiment, the transmitting coil and the receiving coil can be positioned such that the receiving coil is within the near field of the magnetic field of the transmitting coil. The near field can be based within the Fraunhofer region, which can be approximately within $1/2\pi$ times the wavelength of the electromagnetic field.

One advantage of placing the receiving coil within the near field for wireless energy transfer is to reduce an amount of energy that may be radiated or leaked from the wireless transfer coils 210 and 220, e.g. energy not received at the receiving coil 220. In one embodiment, energy in a magnetic field falls off as the inverse squared of a distance ($1/d^2$) between the transmitting coil 210 and the receiving coil 220 within the near field. In one example, magnetic resonant coupling can be used to transfer energy at relatively high energy levels between the transmitting coil 210 and the receiving coil 220 and to minimize or reduce energy leaking away from the wireless transfer coils 210 and 220.

Another advantage of using a near field or a non-radiating field for wireless energy transfer can be that the near field or the non-radiating field can be used in areas adjacent to biological material, such as humans or other biological entities, with minimal or no effects to the biological material from the wireless energy transfer. In another embodiment, a wireless transfer station, such as in FIG. 1, can use a radio frequency (RF) signal, ultrasound, and/or laser beams to wirelessly transfer energy and/or data between a transmitting device and a receiving device.

Figure 3A:
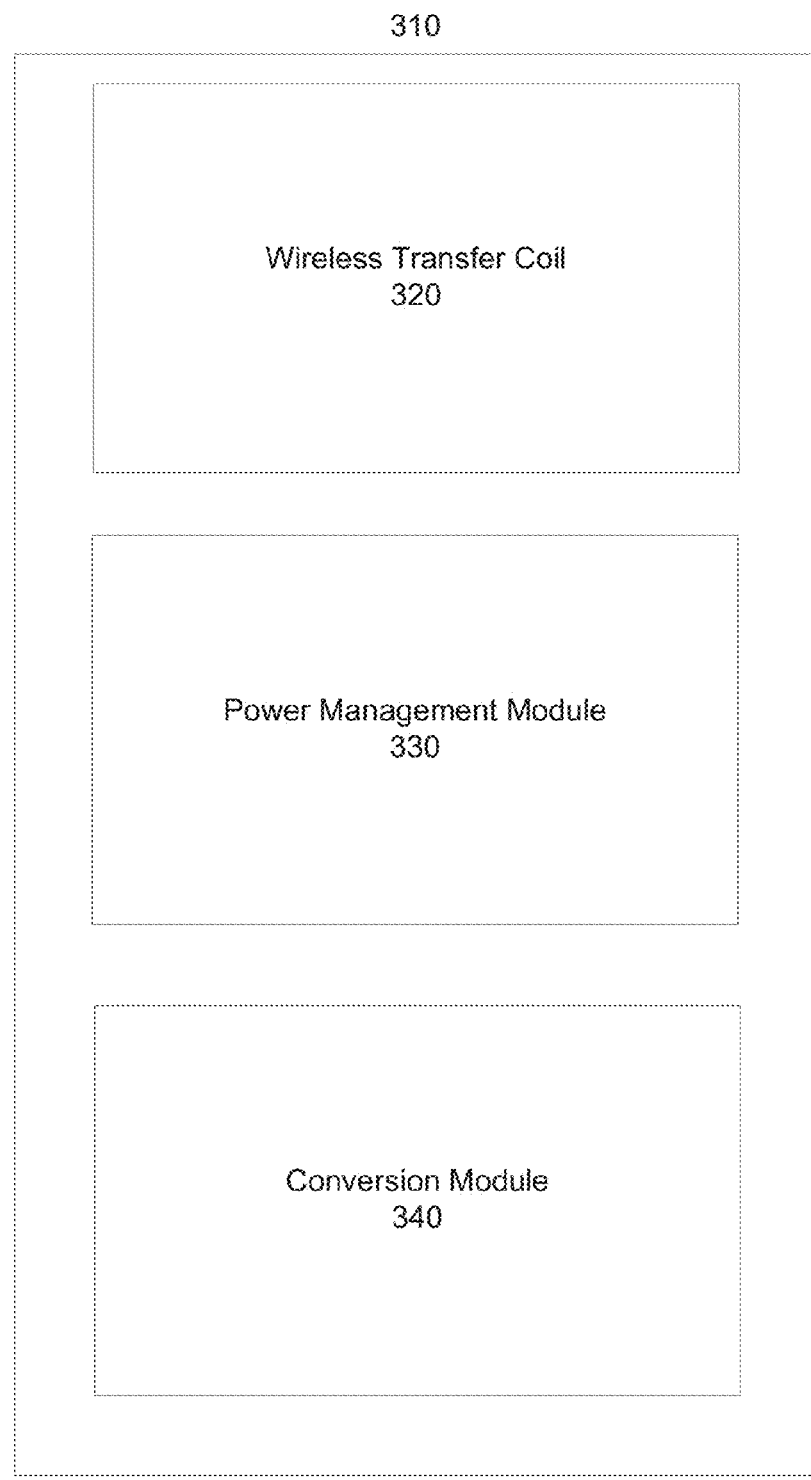
FIG. 3a depicts a wireless transfer station in accordance with an example.

FIG. 3a shows a wireless transfer station 310 that can include: a wireless transfer coil 320, a power management module 330, and a conversion module 340. In one embodiment, the wireless transfer coil 320 can be used for resonance coupling and/or induction coupling. In one example, the conversion module 340 can be coupled to the wireless transfer coil 320 and used to switch the wireless transfer coil 320 from a resonance mode (i.e. transferring wireless energy and/or data using magnetic resonance coupling) to an induction mode (i.e. transferring wireless energy and/or data using magnetic induction coupling), or vice versa.

In one embodiment, the wireless transfer coil 320 of the wireless transfer station 310 can be used for transmitting wireless energy and/or receiving wireless energy. In one example, the conversion module 340 can be coupled to the wireless transfer coil 320 and used to switch the wireless transfer coil 320 from a receiving mode (i.e. receiving wireless energy and/or data) to a transmitting mode (i.e. transmitting wireless energy and/or data), or vice versa.

In one embodiment, when the conversion module 340 of the wireless transfer station 310 is in the transmitting mode, the conversion module 340 or the power management module 330 can convert energy received from an energy source (such as a power outlet or a battery) at a selected voltage into a high frequency alternating current and transmit the high frequency alternating current to a wireless transfer coil of another wireless transfer station. The high frequency alternating current can flow through one or more loops of the wireless transfer coil 320 and create a varying magnetic field that can induce a current in the other wireless transfer coil. In another embodiment, when the conversion module 340 is switched to the receiving mode, a varying magnetic field from another wireless transfer station can induce an alternating current flowing through the one or more loops of the wireless transfer coil 320. The current flowing through the one or more loops can be converted into a direct current (DC) by the conversion module 340 or the power management module 330 and directed to a battery coupled to the wireless transfer station 310 or a device that is electrically coupled to the wireless transfer station 310.

In one embodiment, each wireless transfer coil 320 of a wireless transfer station 310 can be coupled to a separate conversion module 340. In another embodiment, one or more conversion modules 340 can be coupled to one or more selected groups of wireless transfer coils 320. One advantage of using a conversion module 340 for switching a wireless transfer coil 320 between transmitting mode and receiving mode can be to reduce a complexity of design and/or size of a wireless transfer station 310 by reducing a number of wireless transfer coils 320 used to transmit and/or receive wireless energy. Another advantage of using a conversion module 340 for switching a wireless transfer coil between a transmitting mode and receiving mode is to provide a dual functionality to a wireless transfer station of both transmitting and receiving wireless energy.

Figure 3B:
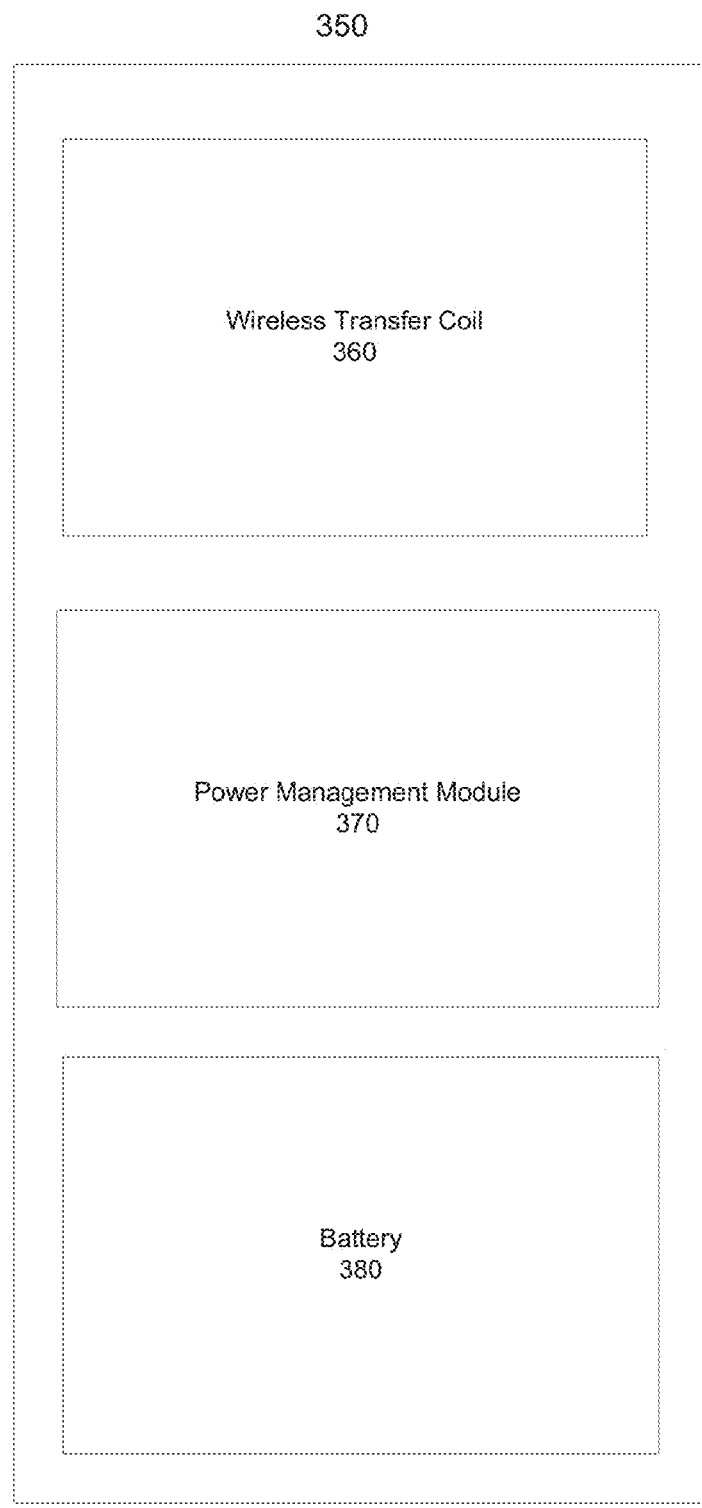
FIG. 3b depicts another wireless transfer station in accordance with an example.

FIG. 3b illustrates a wireless transfer station 350. FIG. 3b further illustrates that the wireless transfer station 350 can include: a wireless transfer coil 360; a power management module 370; and a battery 380. The battery 380 can comprise a plurality of batteries, such as rechargeable batteries. In one example, the power management module 370 can convert energy received using the wireless transfer coil 360 from an energy source, such as another wireless transfer station or an alternating current (AC) energy outlet, to a selected current level at a selected voltage level to provide a selected wattage level. In one embodiment, the power management module can transfer the converted energy to the battery 380 to store the energy.

Figure 3C:
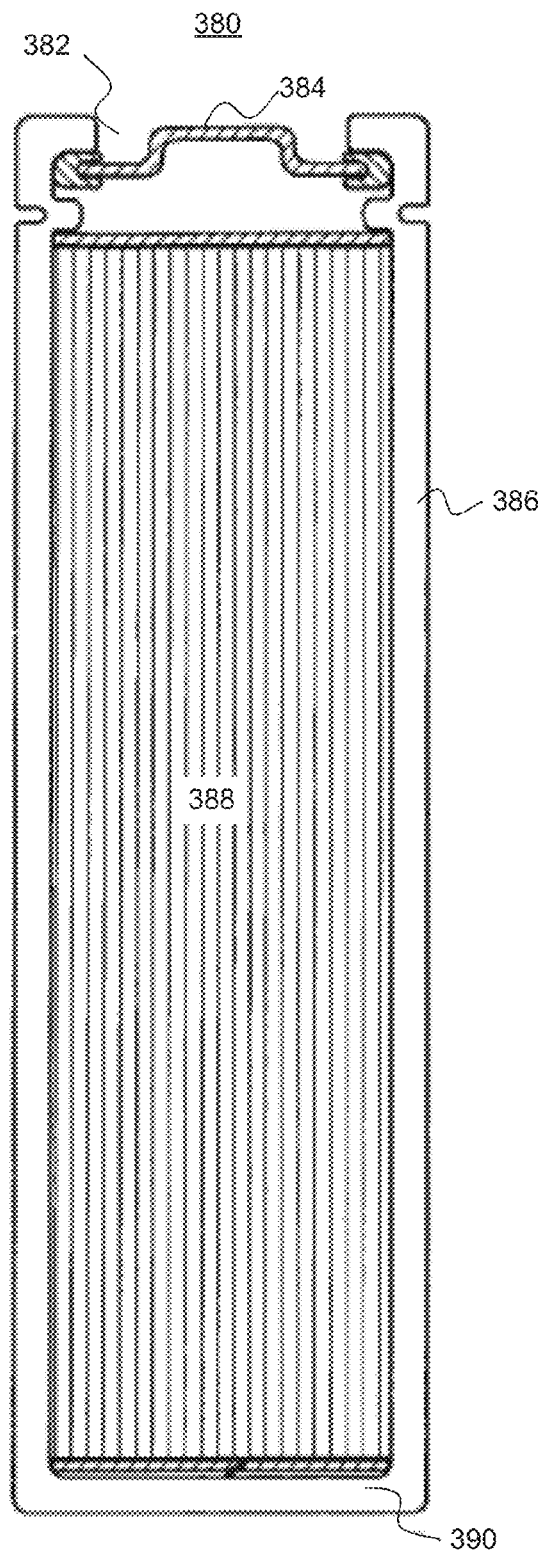
FIG. 3c depicts a cross-sectional view of a battery in accordance with an example.

FIG. 3c shows a cross-sectional view of a battery 380, for example a lithium ion battery utilizing an 18650 battery form-factor. The battery 380 can include: a case 386, such as a cylindrical case; one or more electrodes 388, and a cap 384. In one embodiment, the case 386 can be made of a metal, such as nickel-plated steel, that can be non-reactive with battery materials, such as an electrolyte or the one or more electrodes 388. In one embodiment, a bottom surface 390 of the case 386 can be seamlessly integrated with the remainder of the case 386. In one embodiment, a top end 382 of the case 386 can be open ended. In another embodiment, the cap 384 can be located at the top end 382 of the case 386. In another embodiment, the top end 382 can be a positive electrical terminal of the battery 380 and the bottom end 390 can be a negative electrical terminal. In one example, the positive electrical terminal and the negative electrical terminal of the battery 380 can be connected to a wireless transfer station to provide energy to the wireless transfer station. In another embodiment, a plurality of batteries can be connected in series and/or in parallel. In one embodiment, the battery 380 can be connected to a power management module, such as the power management modules in FIGS. 3a and 3b.

Figure 4:
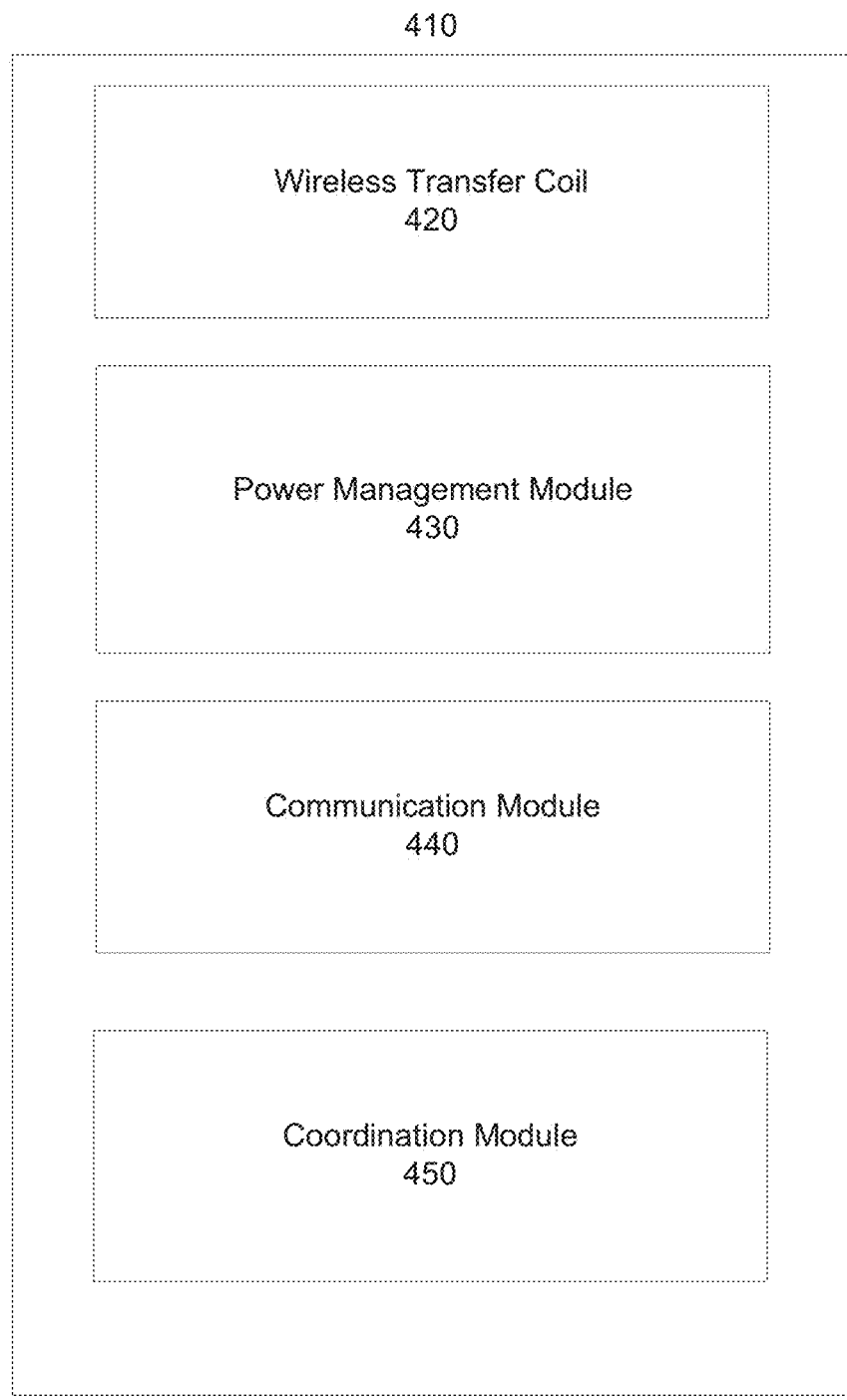
FIG. 4 depicts a wireless transfer station in accordance with an example.

FIG. 4 shows a wireless transfer station 410 that can include: a wireless transfer coil 420, a power management module 430, a communications module 440, and/or a coordination module 450. In one embodiment, the wireless transfer station 410 can communicate with one or more other wireless transfer stations or one or more devices using the communication module 440.

In one embodiment, the communication module 440 of the wireless transfer station 410 can use a communications network to communicate the data to a device and/or another wireless transfer station. In another embodiment, the communications network can be a cellular network that may be a 3GPP LTE Rel. 8, 9, 10, 11, or 12 or IEEE 802.16p, 802.16n, 802.16m-2011, 802.16h-2010, 802.16j-2009, 802.16-2009. In another embodiment, communications network can be a wireless network (such as a wireless fidelity network (Wi-Fi)) that may follow a standard such as the Institute of Electronics and Electrical Engineers (IEEE) 802.11-2012, IEEE 802.11ac, or IEEE 802.11ad standard. In another embodiment, the communications network can be a Bluetooth connection such as Bluetooth v1.0, Bluetooth v2.0, Bluetooth v3.0, or Bluetooth v4.0. In another embodiment, the communications network can be a ZigBee connection such as IEEE 802.15.4-2003 (ZigBee 2003), IEEE 802.15.4-2006 (ZigBee 2006), IEEE 802.15.4-2007 (ZigBee Pro).

In one embodiment, the wireless transfer station 410 can transfer energy to one or more other wireless transfer stations, receive energy from one or more other wireless transfer stations, and/or communicate data or information with one or more other wireless transfer stations. In another embodiment, the coordination module 450 of the wireless transfer station 410 can coordinate when energy is transferred between wireless transfer stations and/or when data is communicated between wireless transfer stations. In another embodiment, the coordination module 450 can use the communications module 440 to communicate with one or more other wireless transfer stations to coordinate energy and/or data transfer between the wireless transfer station 410 and the one or more other wireless transfer stations.

One advantage of transferring energy and/or data using a wireless transfer station 410 is to provide a single connection point between the wireless transfer station 410 and other wireless transfer stations and/or other devices. Another advantage of transferring energy and/or data using the wireless transfer station 410 can be to enable a single step for both transferring energy between the wireless transfer station 410 and other wireless transfer stations and communicating or synchronizing data communicated between the wireless transfer station 410 and other wireless transfer stations. In one example, when a first wireless transfer station (such as a wireless transfer station integrated into a medical cart) is located adjacent to a second wireless transfer station (such as a wireless transfer station integrated into a plate mounted to a wall or a floor mat), the first wireless transfer station can both receive energy from the second wireless transfer station and synchronize information with the second wireless transfer station.

In one embodiment, the coordination module 450 can communicate with a conversion module, as in FIG. 3a, to coordinate when one or more wireless transfer coils 420 of the wireless transfer station 410 can transmit and/or receive wireless energy and/or data. In one example, the coordination module 450 communicates with a conversion module, as in FIG. 3a, to coordinate transmitting and/or receiving wireless energy and/or data by coordinating when one or more wireless transfer coils 420 are in a transmitting mode or a receiving mode, as discussed in the preceding paragraphs.

Figure 5A:
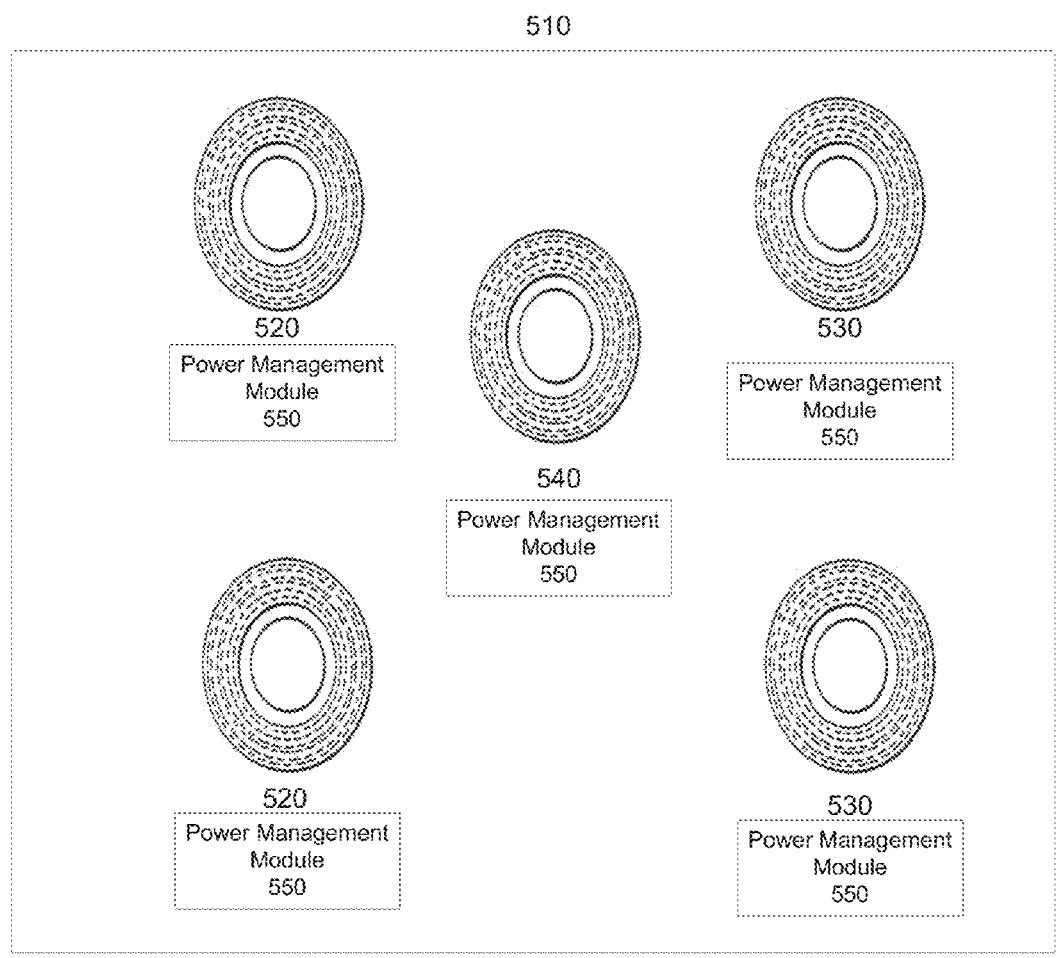
FIG. 5a depicts a wireless transfer station that includes one or more resonant wireless transfer coils and/or one or more induction wireless transfer coils in accordance with an example.

FIG. 5a shows a wireless transfer station 510 that includes one or more resonant wireless transfer coils 520 and/or one or more induction wireless transfer coils 530. In one example, the wireless transfer station 510 can have a resonant wireless transfer coil 520 and can transfer energy to a resonant wireless transfer coil of a first wireless transfer station and can have an induction wireless transfer coil 530 and can transfer energy to an induction wireless transfer coil of a second wireless transfer station. One advantage of the wireless transfer station having both resonant wireless transfer coils 520 and induction wireless transfer coils 530 can be to provide energy and/or data to wireless transfer stations and/or devices with only one of the resonant wireless transfer coils or the induction wireless transfer coils, thereby enabling more devices to transfer energy to the wireless transfer station.

In one embodiment, a device or another wireless transfer station can include one or more resonant wireless transfer coils and/or one or more induction wireless transfer coils. In one embodiment, the device or the other wireless transfer station receiving energy from the wireless transfer station 510 can select whether to receive wireless energy from the one or more resonant wireless transfer coils 520 or the one or more induction wireless transfer coils 530 of the wireless transfer station 510. In another embodiment, the wireless transfer station 510 can be configured to select whether to transmit wireless energy using the one or more resonant wireless transfer coils 520 or the one or more induction wireless transfer coils 530. In one example, a resonant transmitting coil and a resonant receiving coil pair can have a higher energy transfer efficiency than an induction transmitting coil and an induction receiving coil pair. In this example, when the device or the other wireless transfer station includes a resonant receiving coil, the other wireless transfer station and/or the device or the wireless transfer station 510 can be configured to use one or more resonant wireless transfer coils to perform an energy transfer.

In one embodiment, the one or more resonant wireless transfer coils 520 and/or the one or more induction wireless transfer coils 530 can be transmitting coils and/or receiving coils. In another embodiment, the wireless transfer station 510 can include one or more repeater coils 540. In one example, the repeater coil 540 can enhance wirelessly transmitted energy of a transmitting coil, e.g. providing additional transmission energy. In another example, the repeater coil 540 can receive the wireless energy from a transmitting coil and relay or retransmit the received energy to another repeater coil 540 or to a receiving coil. The repeater coils can be configured as inductive repeater coils or resonant repeater coils, and associated with transmit coils and receive coils of the same kind.

In one embodiment, the one or more resonant wireless transfer coils 520, the one or more induction wireless transfer coils 530, and/or the repeater coil 540 can include a power management module 550 configured to covert energy from an energy source to a varying magnetic field. In another embodiment, the one or more resonant wireless transfer coils 520, the one or more induction wireless transfer coils 530, and/or the repeater coil 540 can be coupled to a power management module 550 configured to convert a magnetic field into energy, such as energy at a selected current level, a voltage level, a wattage level, and/or an amperage level, and transfer the energy to a battery of the wireless transfer station 510 or a device coupled to the wireless transfer station 510.

Figure 5B:
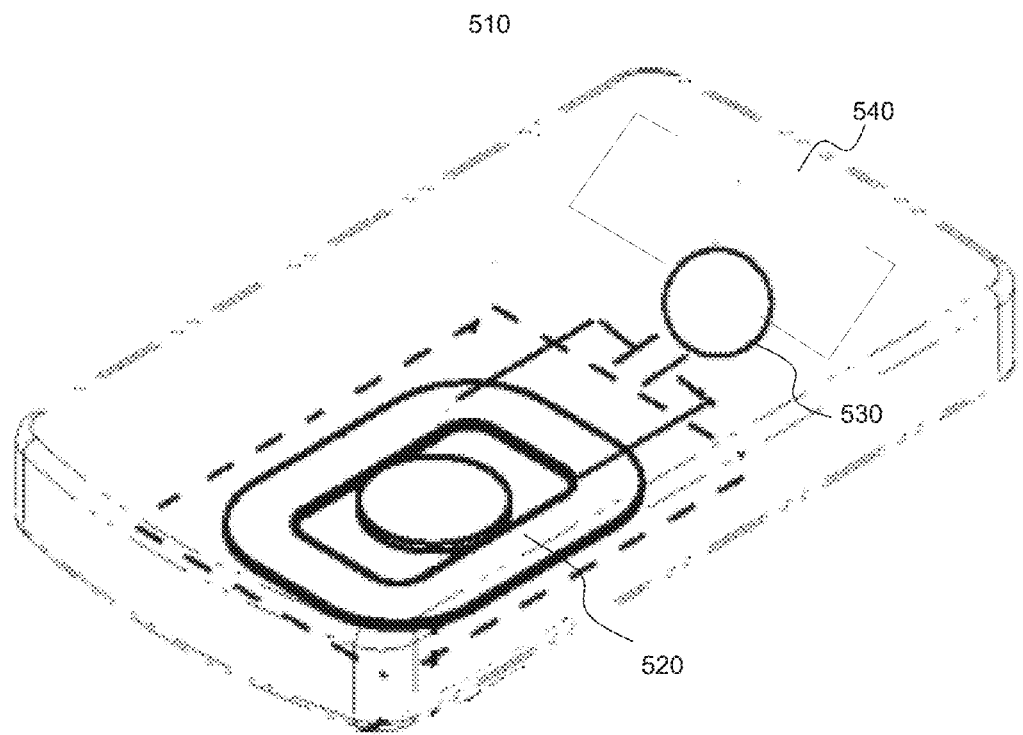
FIG. 5b depicts a wireless transfer station in accordance with an example.

FIG. 5b illustrates one exemplary embodiment of the wireless transfer station 510. In one embodiment, the wireless transfer station 510 can be a stand-alone device used to transfer wireless energy to other devices. In another embodiment, the wireless transfer station 510 can include a wireless transfer coil 520 and a power management module 530. In another embodiment, the wireless transfer station 510 can direct energy received at the wireless transfer coil 520 using the power management module 530 to a device coupled to the wireless transfer station 510.

In another embodiment, the wireless transfer station 510 can transfer the energy received at the wireless transfer coil 520 to the coupled device using physical electrical contacts. In another embodiment, the wireless transfer station 510 can transfer the energy to the coupled device using the wireless transfer coil 520. In one embodiment, the wireless transfer station 510 can store received energy at a battery 540.

Figure 5C:
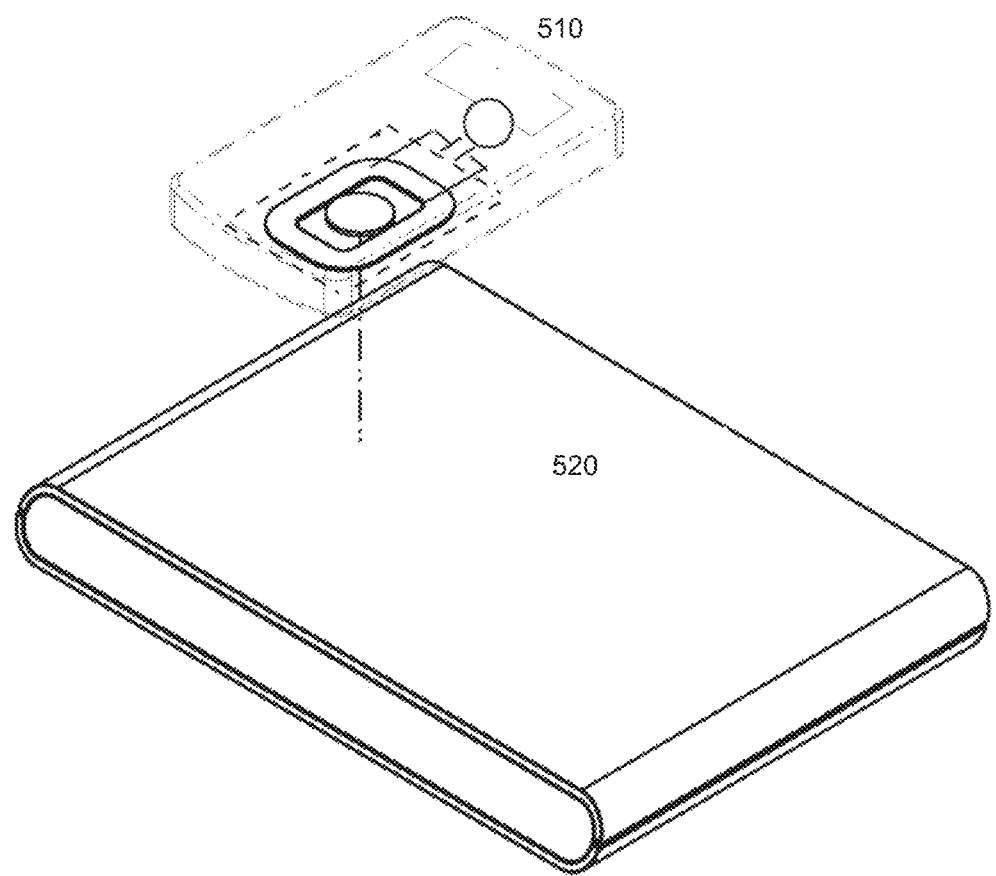
FIG. 5c depicts a wireless transfer station integrated into an object in accordance with an example.
Figure 5D:
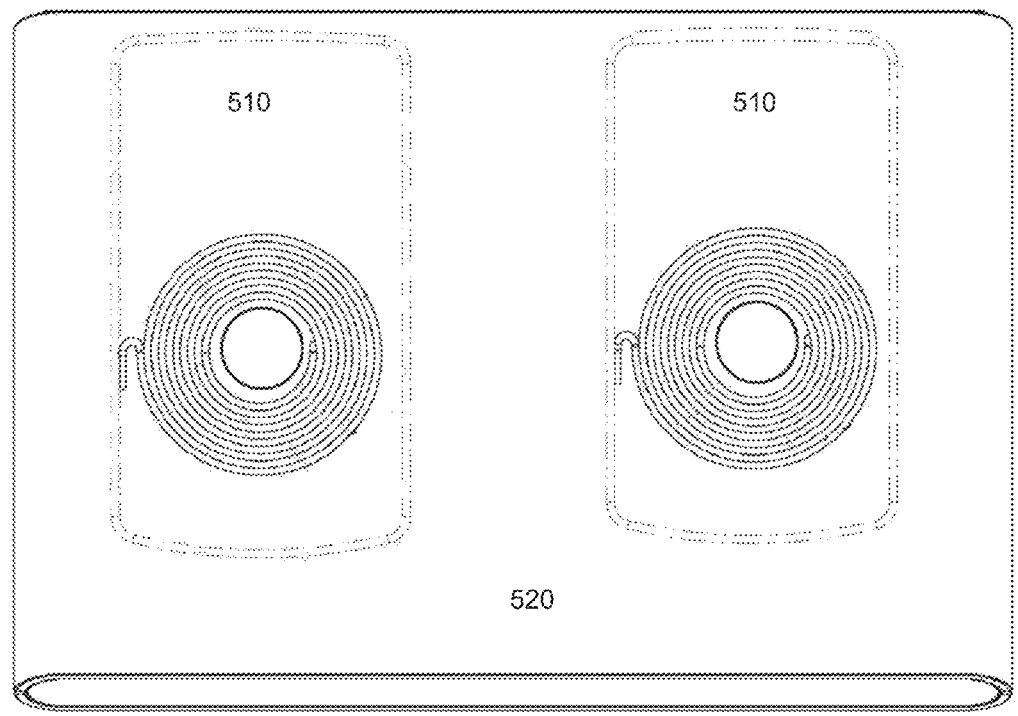
FIG. 5d depicts a plurality of wireless transfer stations integrated into an object in accordance with an example.

FIG. 5c illustrates one exemplary embodiment of the wireless transfer station 510 integrated into an object 520. In one embodiment, the object 520 that the wireless transfer station 510 can be integrated into can be an electronic device, such as a medical device or a wireless energy battery pack. In one example, the wireless transfer station 510 can be integrated into a medical infusion pump and provide energy to the medical infusion pump. In another embodiment, the object 520 can be integrated into a medical cart (such as a work surface of the medical cart), a floor mat, a floor surface, a plate mounted to a wall, a wall surface, chair railing, a room railing, a ceiling tile, a ceiling surface, and so forth. FIG. 5d illustrates that a plurality of wireless transfer stations 510 can be integrated into an object 520. FIG. 5d is the same as FIG. 5c in all other aspects.

Figure 6:
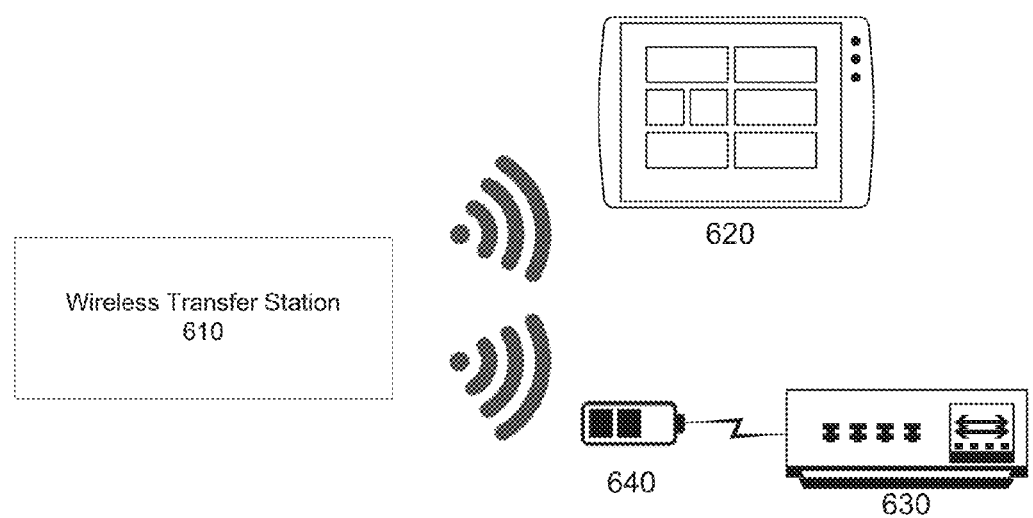
FIG. 6 depicts a wireless transfer station that can provide energy to one or more wirelessly powered electronic devices and/or one or more rechargeable batteries coupled to a device in accordance with an example.

FIG. 6 shows a wireless transfer station 610 that can provide energy to one or more non-wire powered electronic devices 620 and/or one or more rechargeable batteries 640 coupled to a device 630. In another embodiment, the wireless transfer station 610 can provide energy to different types of non-wire powered electronic devices, such as a monitoring device, a computing device, a medical device, and so forth. In one example, the wireless transfer station 610 can provide a unified energy source for the devices 620 and 630 and/or the one or more rechargeable batteries 640 coupled to the device 630. In one embodiment, a unified energy source can be a power source that can provide power to a device, a wireless transfer station, and/or a battery without using different power connectors to provide the power to the device, the wireless transfer station, and/or the battery. In one embodiment, the wireless transfer stations can include an integrated wireless energy coil and a physical electrical energy connection terminal. In another embodiment, the wireless transfer station 610 can transfer energy via an electrical energy connection terminal and/or an integrated wireless transfer coil.

Figure 7A:
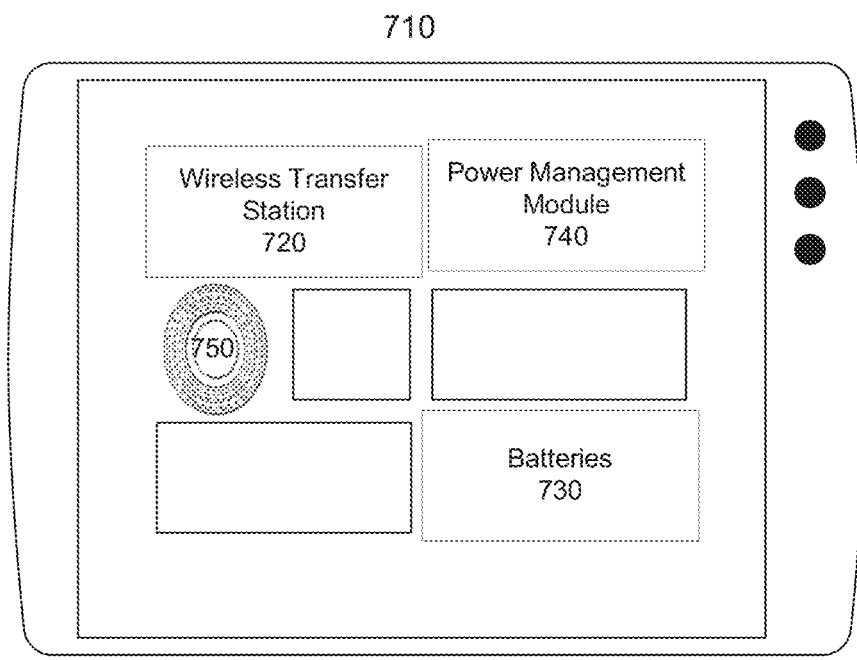
FIG. 7a depicts a device with a wireless transfer station coupled to a device or integrated into the device in accordance with an example.

FIG. 7a shows a device 710 with a wireless transfer station 720 coupled to the device 710 or integrated into the device 710. In one embodiment, the wireless transfer station 720 can be configured to provide energy to batteries 730 of the device 710 and the batteries 730 can provide energy to the device 710. In another embodiment, the wireless transfer station 720 can be configured to provide energy directly to the device 710, e.g. without using batteries. In one example, a power management module 740 can provide energy directly to the device 710 by receiving energy at a wireless transfer coil 750 of the wireless transfer station 710 from a wireless transfer coil of another wireless transfer station and direct the energy via the power management module 740 to the device 710 and/or the batteries 730.

Figure 7B:
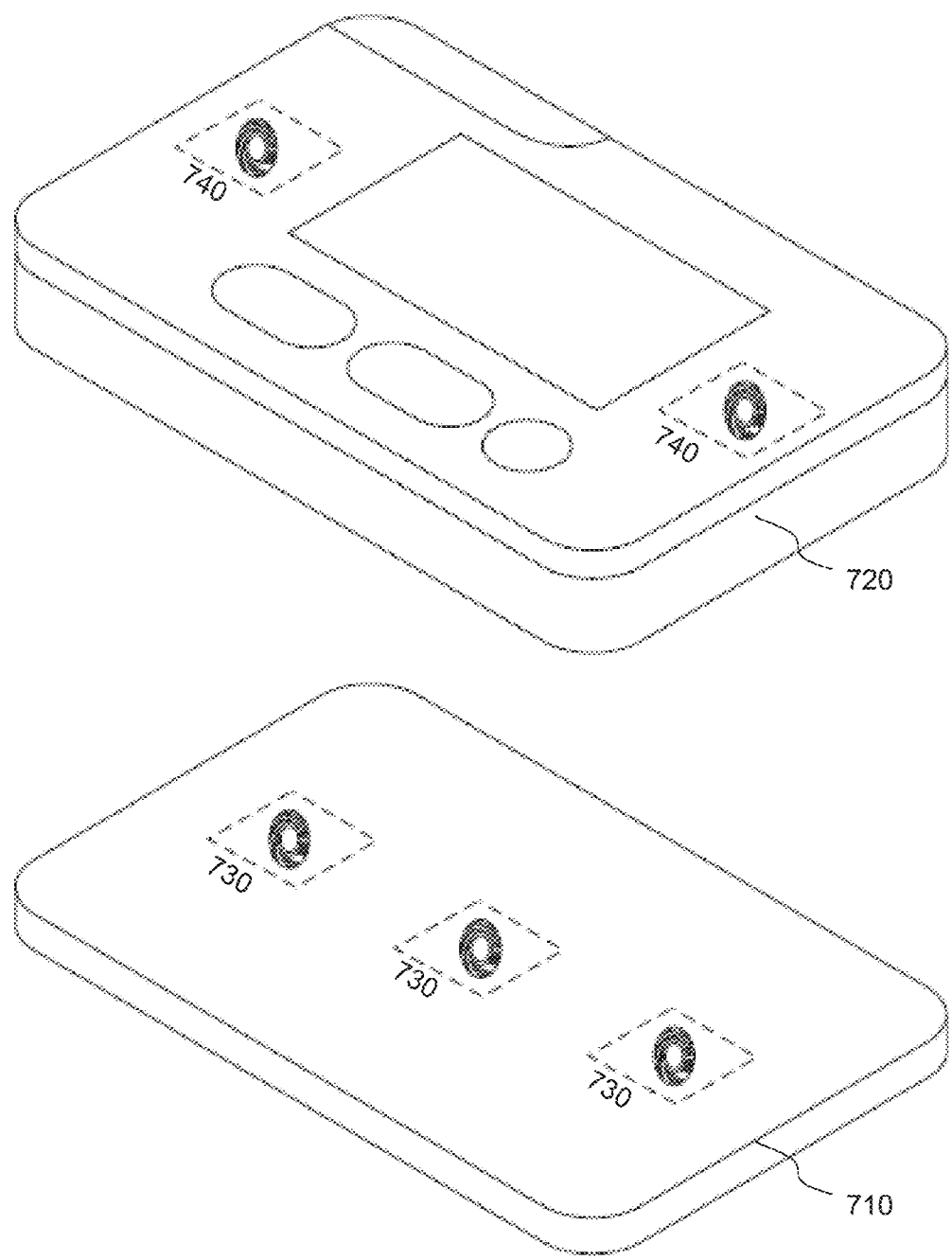
FIG. 7b depicts a wireless transfer station with a plurality of wireless transfer coils configured to transfer energy and/or data to an electronic device in accordance with an example.

FIG. 7b illustrates a wireless transfer station 710 with a plurality of wireless transfer coils 730 configured to transfer energy and/or data to an electronic device 720, such as a medical device. The medical device can include one or more integrated wireless transfer stations 740. In one embodiment, the electronic device 720 can be located adjacent to the wireless transfer station 710. For example, a bottom surface of the electronic device 720 can abut a top surface of the wireless transfer station 710.

Wireless Transfer Station Incorporated into Medical Cart

In one embodiment, the wireless transfer station or one or more components of the wireless transfer station can be incorporated into a device. The device can be: a wheeled medical cart; a platform coupled the wheeled medical cart; a platform integrated into the wheeled medical cart; and/or a device coupled the wheeled medical cart.

FIGS. 8a, 8b, and 8c show a wheeled medical cart 810 with different configurations of integrated wireless transfer stations 820, 830, and 840, respectively. FIG. 8a shows a wheeled medical cart 810 with a plurality of wireless transfer stations 820 integrated into a selected area 852 of a work surface 850 of the wheeled medical cart 810. FIG. 8b shows a wheeled medical cart 810 with a plurality of wireless transfer stations 830 integrated into a work surface 860 of the wheeled medical cart 810. The wheeled medical cart 810 of FIG. 8b is the same as the wheeled medical cart 810 in FIG. 8a in all other regards. FIG. 8c shows a wheeled medical cart 810 with one or more of wireless transfer stations 840 integrated into a device holder 870 of the wheeled medical cart 810. The wheeled medical cart 810 of FIG. 8c is the same as the wheeled medical carts 810 in FIGS. 8a and 8b in all other regards.

In one embodiment, the wheeled medical cart 810 can have one or more attached work surfaces 850 or 860. In one example, the one or more work surfaces 850 or 860 and/or device holder 870 of the wheeled medical cart can include one or more integrated or coupled wireless transfer coils, such as one or more transmitting coils, one or more repeater coils, and/or one or more receiving coils. In another embodiment, the one or more work surfaces 850 or 860 and/or device holder 870 can have one or more selected areas for other devices, such as medical devices and/or mobile devices, to be placed on the one or more work surfaces 850 or 860 and/or device holder 870 and receive wireless energy.

In one embodiment, the device holder 870 can be designed to hold one or more devices at selected alignments to orient the one or more devices to receive energy from one or more of wireless transfer stations 840. In one example, the device holder 870 can be integrated into the wheeled medical cart 810 and the device holder 870 can hold and orient one or more medical devices to receive wireless energy using wireless transfer stations coupled to the medical devices and/or wireless transfer stations integrated into the medical devices.

In one embodiment, the wheeled medical cart 810 can include one or more electrical systems and/or one or more devices coupled to the wheeled medical cart 810. In another embodiment, the wheeled medical cart 810 can use one or more wireless transfer stations 880 to power the one or more electrical systems and/or the one or more devices. In another embodiment, the one or more wireless transfer stations 880 can receive wireless energy while attached to the wheeled medical cart. In another embodiment, the one or more wireless transfer stations 880 can be removed from the wheeled medical cart and can be attached to another wireless transfer station or be located adjacent to the wireless transfer station and receive wireless energy.

Figure 9:
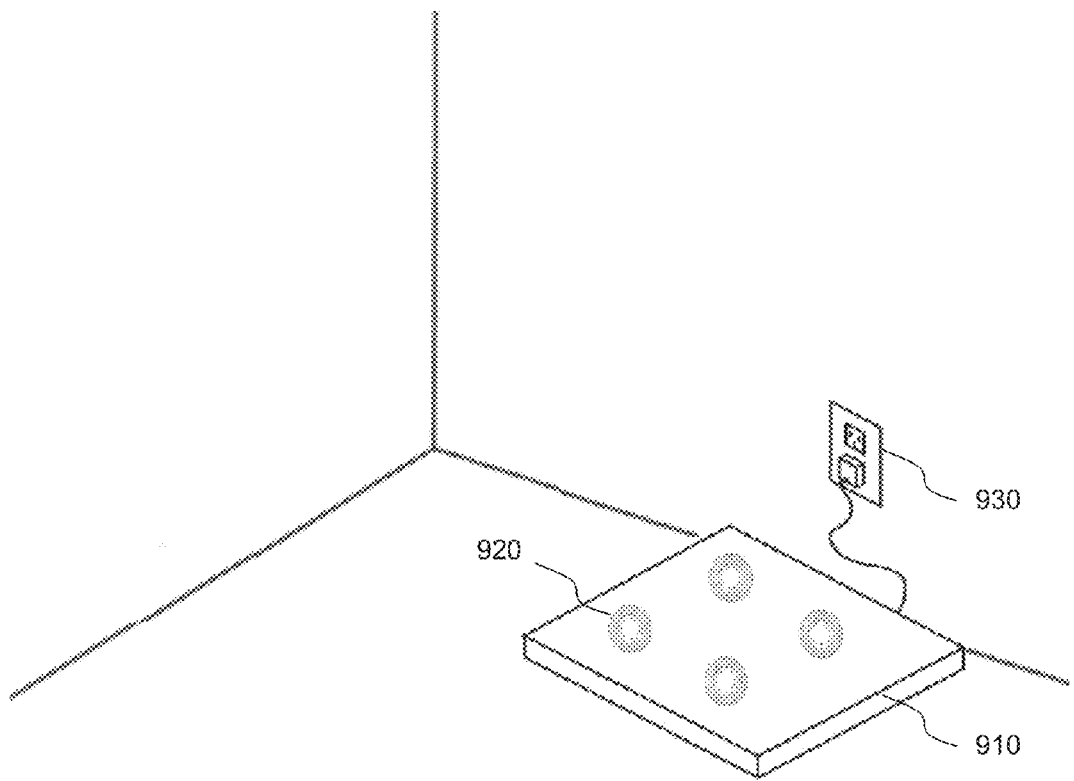
FIG. 9 depicts a floor mat with one or more integrated wireless transfer stations in accordance with an example.

FIG. 9 shows one exemplary embodiment of floor mat 910 with one or more integrated wireless transfer stations 920. In one embodiment, the integrated wireless transfer stations 920 can receive energy and/or data from an outlet 930. In one embodiment, the outlet 930 can be a wall outlet and the integrated wireless transfer stations 920 can receive alternating current (AC) from the outlet 930. In another embodiment, the outlet 930 can be a data outlet, such as an Ethernet outlet, and the integrated wireless transfer stations 920 can receive data from the outlet 930.

In another embodiment, the one or more integrated wireless transfer stations 920 can include one or more wireless transfer coils to transfer energy from the wireless transfer station 920 to another wireless transfer station. In one example, a wireless transfer station coupled to a wheeled medical cart can be moved into a location in proximity or adjacent to the wireless transfer station integrated 920 into the floor mat 910 and receive energy from the one or more wireless transfer stations 920 integrated into the floor mat 910.

Figure 10:
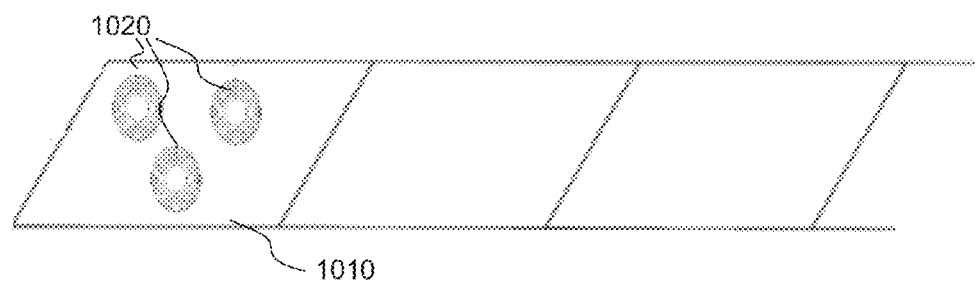
FIG. 10 depicts a flooring surface with one or more integrated wireless transfer stations in accordance with an example.

FIG. 10 shows one exemplary embodiment of a flooring surface 1010 with one or more integrated wireless transfer stations 1020. In another embodiment, the one or more integrated wireless transfer stations 1020 can include one or more wireless transfer coils. In another embodiment, the flooring surface 1010 can be a flooring tile with the one or more integrated wireless transfer stations 1020 integrated into the flooring tile. In another embodiment, the one or more integrated wireless transfer stations 1020 can be coupled to the flooring surface, such as attached to an outer surface of a flooring tile.

Figure 11:
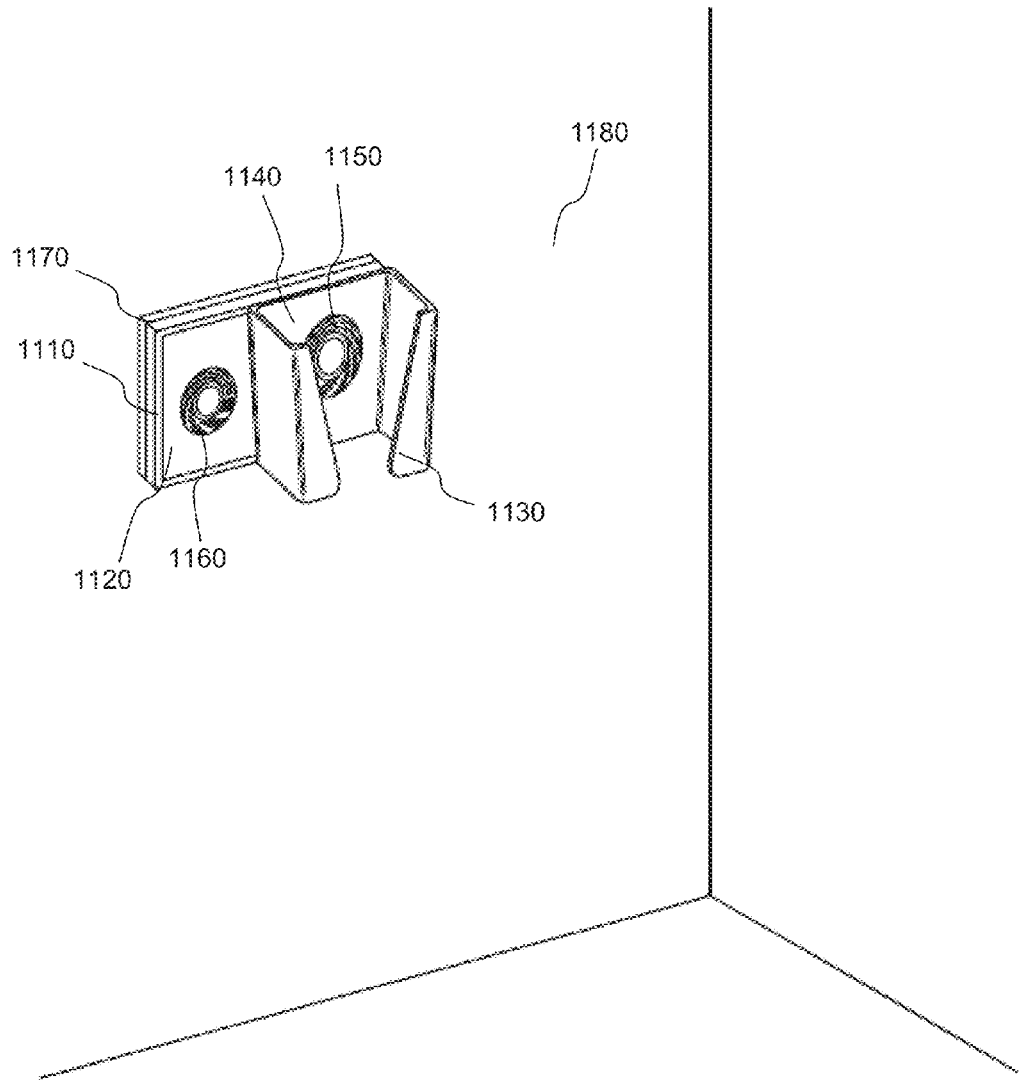
FIG. 11 depicts a plate mounted to a wall with one or more integrated wireless transfer stations in accordance with an example.

FIG. 11 shows one exemplary embodiment of a plate 1110 mounted to a wall 1180 with one or more integrated wireless transfer stations 1120. In another embodiment, the one or more integrated wireless transfer stations 1120 can include one or more wireless transfer coils 1160. In another embodiment, the plate 1110 can be integrated into the wall 1180. In another embodiment, the one or more integrated wireless transfer stations 1120 can be coupled to the wall 1180, such as attached to an inner surface of the wall 1180. In another embodiment, a receptacle 1130 can be attached to the plate 1110. In another embodiment, the receptacle 1130 can receive a device, such as a medical device, or another wireless transfer station. In another embodiment, one or more wireless transfer stations 1140 can be coupled to the receptacle 1130 and the one or more wireless transfer stations 1140 can be used to transfer energy and/or data with the device or the other wireless transfer station, such as by using a wireless transfer coil 1150.

In another embodiment, a plate 1110 can be attached to a mounting plate 1170 that is attached to the wall 1180. One advantage of attaching the plate 1110 to the mounting plate 1190 can be that the plate 1110 can be easily and/or quickly removed from the mounting plate 1170 for maintenance, upgrades, replacement, and so forth. In one embodiment, the plate 1110 can be attached to the mounting plate 1170 using one or more fasteners or connectors, such as hooks, quick connectors, screws, bolts, and so forth.

In one embodiment, the wireless transfer station can monitor an amount of energy and/or data transmitted by a wireless transfer coil and/or an amount of energy and/or data received by the wireless transfer coil. In one example, a first wireless transfer station with a receiving coil can communicate energy information to a second wireless transfer station with a transmitting coil, using a communications module as discussed in the preceding paragraphs. The energy information can include: voltage level information, current draw level information, energy level information of the energy received at the receiving coil, energy level information of the energy transmitted from the transmitting coil, internal temperature information, ambient temperature information, or other types of desired metrics.

In one embodiment, the wireless transfer station can adjust an amount of energy transmitted from a wireless transfer coil of a wireless transfer station to another wireless transfer coil of another wireless transfer station based on the energy information. In one example, if a device with an integrated or coupled wireless transfer station requires 5 volts (V) and 2 amps (A) of energy and is currently receiving a voltage level or an amperage level at a level above or below a selected energy level range (such as a voltage range and/or a current range), the device or the coupled wireless transfer station can communicate the energy information to the wireless transfer station. In this example, the wireless transfer station can adjust the energy transferred from the wireless transfer coil to the other wireless transfer coil to bring the energy level range received at a wireless transfer coil to a level within a selected energy level range.

In another embodiment, a wireless transfer station can be a communication hub between multiple devices and/or other wireless transfer stations. In one example, the wireless transfer station can be integrated into a medical cart. The medical cart can receive data from a first device using a communication module (as discussed in the preceding paragraphs) and relay the data to another wireless transfer station, such as a wireless transfer station attached to a wall or floor.

In one embodiment, the wireless transfer station can regulate an amount of energy received by one or more other wireless transfer stations. In one example, when a first wireless transfer station uses a transmitting coil for a transfer of energy and/or data, the first wireless transfer station can control an amount of energy received at a second wireless transfer station by detuning a frequency of the transmitting coil by a selected amount. In another example, when a first wireless transfer station uses receiving coils for a transfer of energy and/or data, the first wireless transfer station can control an amount of energy received from a second wireless transfer station by detuning a frequency of the receiving coil by selected amount. In another example, to regulate the amount of energy and/or transferred between the first wireless transfer station and the second wireless transfer station, the first wireless transfer station and/or the second wireless transfer station can adjust a number of winds of a wireless transfer coil used to create an magnetic field or couple with the magnetic field.

Figure 12:
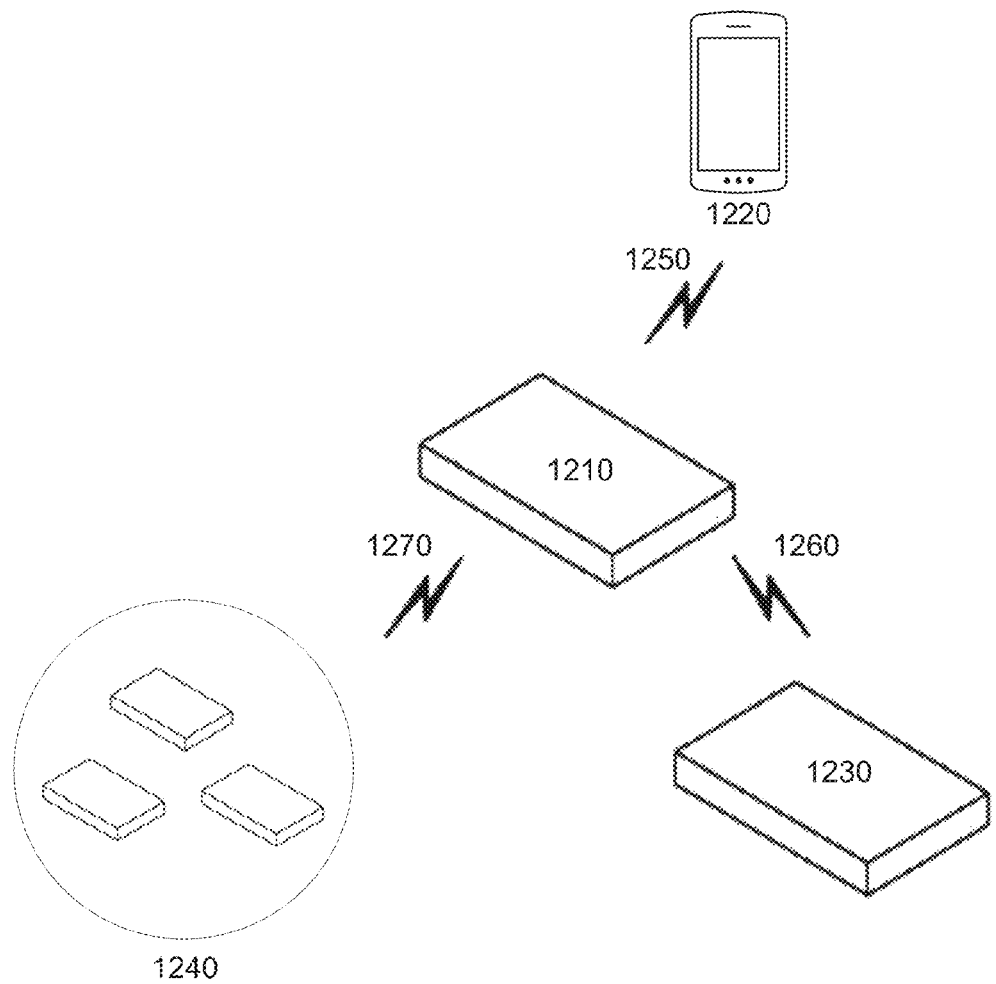
FIG. 12 depicts a wireless transfer station transferring energy or data to a plurality of different devices and other wireless transfer stations in accordance with an example.

FIG. 12 illustrates a wireless transfer station transferring energy and/or data to a plurality of different devices and other wireless transfer stations. In one embodiment, to regulate an amount of energy and/or data received by a device 1220, a wireless transfer station 1230, and/or a selected group of other wireless transfer stations 1240, wireless transfer coils of the device 1220, the wireless transfer station 1230, and/or the selected group of other wireless transfer stations 1240 can be tuned to different frequencies 1250, 1260, and 1270, respectively. In one embodiment, the wireless transfer station 1210 can switch a plurality of wireless transfer coils of the wireless transfer station 1210 to the frequencies 1250, 1260, and 1270 that correspond to the frequencies for the device 1220, the wireless transfer station 1230, and/or the selected group of other wireless transfer stations 1240, respectively, to provide data and/or selected amounts of energy on the frequencies 1250, 1260, and 1270. In one embodiment, the different frequencies 1250, 1260, and 1270 can be different resonant frequencies. In one embodiment, the wireless transfer station 1210 can switch one wireless transfer coil of the wireless transfer station 1210 to different frequencies 1250, 1260, and 1270 that correspond to the frequencies for the device 1220, the wireless transfer station 1230, and/or the selected group of other wireless transfer stations 1240, respectively to provide data and/or selected amounts of energy on the frequencies 1250, 1260, and 1270 for selected periods of time. In one embodiment, a frequency of the wireless transfer coils of the wireless transfer station 1210, the device 1220, the wireless transfer station 1230, and/or the selected group of other wireless transfer stations 1240 can be dynamically adjusted or varied to different selected frequencies. In another embodiment, different amounts of energy and/or data can be transferred on the different frequencies 1250, 1260, and/or 1270. In another embodiment, an amount of energy and/or data transferred on the different frequencies 1250, 1260, and 1270 can be dynamically varied.

In one embodiment, the wireless transfer station 1210 can collect and/or store data and/or energy information of the wireless transfer station 1210, the device 1220, the wireless transfer station 1230, and/or the selected group of other wireless transfer stations 1240. In another embodiment, the wireless transfer station 1210 can analyze the data and/or energy information to determine an amount of energy received and/or used by the wireless transfer station 1210, the device 1220, the wireless transfer station 1230, and/or the selected group of other wireless transfer stations 1240. In another embodiment, the wireless transfer station 1210, the device 1220, the wireless transfer station 1230, and/or the selected group of other wireless transfer stations 1240 can collect and/or store the data and/or energy information.

In one embodiment, the energy information can include: a state of the device 1220, the wireless transfer station 1210 or 1230, and/or the selected group of other wireless transfer stations 1240; a state of a subsystem or module of the device 1220, the wireless transfer station 1210 or 1230, and/or the selected group of other wireless transfer stations 1240; a state of the device 1220, the wireless transfer station 1230, and/or the selected group of other wireless transfer stations 1240 within a coverage area of the wireless transfer station 1210; location information of the device 1220, the wireless transfer station 1230, and/or the selected group of other wireless transfer stations 1240 within the coverage area of the wireless transfer station 1210; a wireless transfer station identification (ID), a device ID, a wireless transfer station subsystem ID or module ID, a usage level of the device 1220, the wireless transfer station 1210 or 1230, and/or the selected group of other wireless transfer stations 1240; and/or health information of the device 1220, the wireless transfer station 1230, and/or the selected group of other wireless transfer stations 1240 within the coverage area of the wireless transfer station 1210. In one embodiment, the health information can be information of an actual full charge capacity of one or more batteries or one or more battery cells of the device 1220, the wireless transfer station 1210 or 1230, and/or the selected group of other wireless transfer stations 1240 compared to a designed capacity of one or more batteries or one or more battery cells of the device 1220, the wireless transfer station 1210 or 1230, and/or the selected group of other wireless transfer stations 1240. In one example, the actual full charge capacity of a battery of the wireless transfer station 1210 can be 16 amp hours and the designed capacity of the battery can be 24 amp hours and the health information can indicate that the actual full charge capacity is below the designed capacity. In another embodiment, the health information can include a battery depletion rate, a number of charge cycles of a battery or group of batteries, an amount of charge a battery or group of batteries received for a charge period, an average charge period for a battery or group of batteries, a remaining battery capacity level of a battery or group of batteries, and so forth.

In one embodiment, selected locations can have wireless transfer stations that can provide energy to one or more devices and/or other wireless transfer stations. The wireless transfer stations can determine an ID of the one or more devices or the other wireless transfer stations and indicate the location of the devices and/or the other wireless transfer stations. In one example, a wheeled medical cart can receive energy from a wireless transfer station at a patient room in a hospital. The wireless transfer station can provide location information of the location of the wheeled medical cart to a central server of the hospital or information technology (IT) department indicating the location of the wheeled medical cart.

In one embodiment, wireless energy and/or data transferred between a first wireless transfer station and a second wireless transfer station can be an alternating current (AC) energy signal. In another embodiment, the first wireless transfer station can send the AC energy signal and to the second wireless transfer station, and the second wireless transfer station can change the AC energy signal into a direct current (DC) energy signal. In one example, the second wireless transfer station can be a wireless energy battery pack. In this example, the wireless energy battery pack can include a built-in charger to convert the AC energy signal to a DC energy signal and transfer the DC energy to one or more batteries or battery cells of the wireless energy battery pack.

Figure 13:
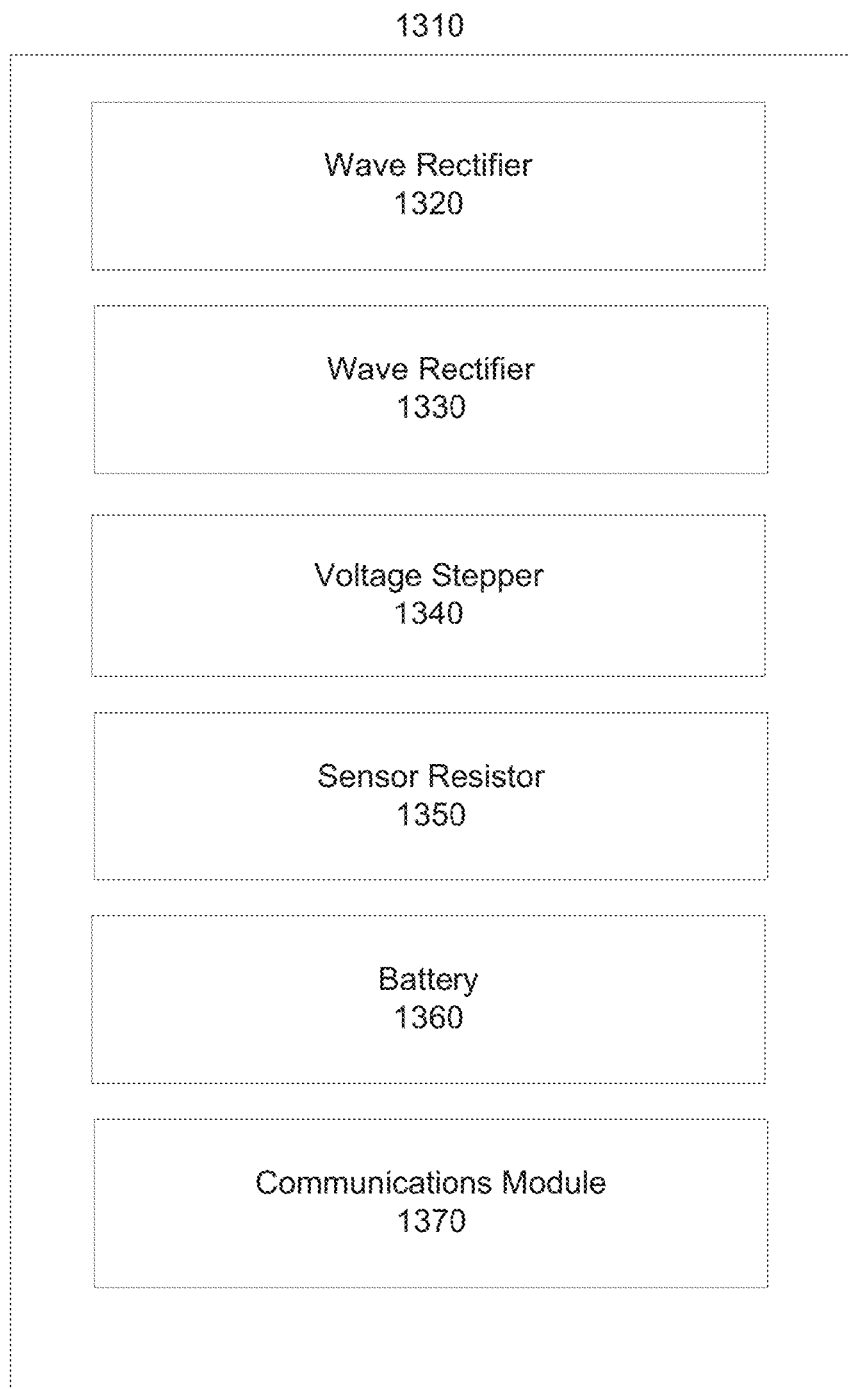
FIG. 13 depicts a wireless transfer station operable to adjust transferred energy in accordance with an example.

FIG. 13 depicts a wireless transfer station 1310 operable to adjust transferred energy. In one embodiment, the wireless transfer station 1310 can include a wave rectifier 1320 to adjust (e.g. step up or step down) a voltage level of transferred energy. In another embodiment, the wireless transfer station 1310 can include a buck converter 1330 and the wave rectifier 1320 can transfer the wireless energy to one or more batteries or one or more battery cells 1360 via the buck converter 1330. In another embodiment, a current level of the wireless transfer station 1310 can be controlled using a voltage stepper 1340 for voltage stepping. In another embodiment, the wireless transfer station 1310 can use a sensor resistor 1350 to measure the current going into the one or more batteries or one or more battery cells 1360. In one example, the wireless transfer station 1310 can communicate voltage level information and/or current level information using a communication module 1370. In this example, the wireless transfer station 1310 can adjust the voltage level and/or current level of the wirelessly transferred energy to a selected level based on the communicated voltage level information and/or current level information. In another embodiment, the wireless transfer station 1310 can use a shunt or voltage stepper 1340 to control an amount of energy transferred between the wireless transfer station 1310 and another wireless transfer station.

In one embodiment, the wireless transfer station can regulate an amount of energy received by one or more other wireless transfer stations. In one example, when a first wireless transfer station uses a wireless transfer coil to transfer energy, the first wireless transfer station can control the amount of energy received at a second wireless transfer station by detuning a frequency of the wireless transfer coil of the first wireless transfer station by a selected amount. In another example, the first wireless transfer station can control the amount of energy received from the second wireless transfer station by detuning a frequency of the wireless transfer coil of the first wireless transfer station by selected amount.

Figure 14:
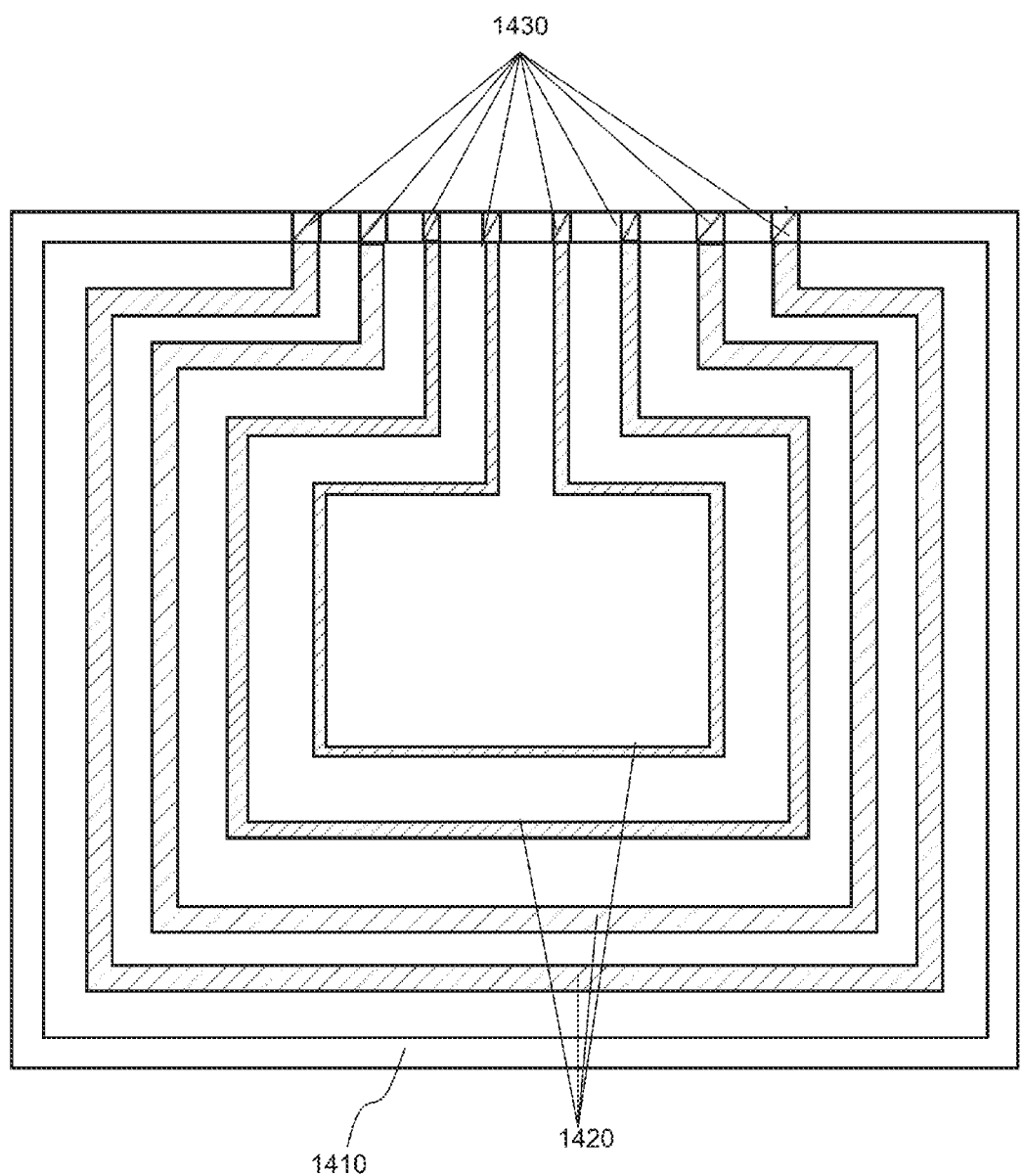
FIG. 14 depicts a wireless transfer coil with a plurality of loops or winds in accordance with an example.

FIG. 14 shows a wireless transfer coil 1410 with a plurality of loops or winds 1420. In one embodiment, an amount of energy transmitted and/or received by the wireless transfer coil 1410 can be adjusted using one or more adjustment modules 1430. In one embodiment, the one or more adjustment modules 1430 can engage or disengage one or more of the plurality of loops 1420 to: effectively vary a size of the wireless transfer coil 1410; change a number of active loops of the wireless transfer coil 1410; change a shape of a magnetic field of the wireless transfer coil 1410;

change an amount of energy transferred using the wireless transfer coil 1410; or enable or disable selected devices from receiving energy and/or data from the wireless transfer coil 1410.

In one embodiment, the one or more adjustment modules 1430 can be one or more switches, such as an impedance matching switch or an on/off switch. In one example, a selected number of the plurality of loops 1420 can be engaged by turning on one or more of the corresponding switches and a selected number of the plurality of loops 1420 can be disengaged by turning off one or more of the corresponding switches.

In one embodiment, a resonant frequency between of the wireless transfer coil 1410 can be dynamically adjusted using the one or more adjustment modules 1430. In one embodiment, the one or more adjustment modules 1430 can be adjustable energy oscillators. In another embodiment, the one or more adjustment modules 1430 can be variable capacitors, variable inductors, and/or variable inductors and the respective capacitance, resistance, and/or inductance can be changed to tune or detune the wireless transfer coil 1410.

In one embodiment, a wireless transfer coil of a first wireless transfer station can have a fixed impedance and/or resonant frequency and an impedance and/or resonant frequency of a second wireless transfer coil of a second wireless transfer station can be adjustable. In another embodiment, the impedance and/or resonant frequency of the wireless transfer coil of the first wireless transfer station and the impedance and/or resonant frequency of the wireless transfer coil of the second wireless transfer station can each be adjustable.

In one embodiment, each wireless transfer station can have a unique station ID associated with the wireless transfer station. In another embodiment, each station ID can be used to associate selected information with each wireless transfer station. In another embodiment, each wireless transfer station and/or each type of wireless transfer station can be configured to have a plurality of different characteristics, such as different form factors, different voltage inputs and/or outputs, different current inputs and/or outputs, and so forth.

In one embodiment, each rechargeable battery or battery cell in a wireless transfer station can have a different battery ID. In another embodiment, one or more types of rechargeable batteries or battery cells in a wireless transfer station can each have different battery IDs. In another embodiment, a wireless transfer station can be coupled to a plurality of different types of devices and/or other wireless transfer stations. In one example, the different types of devices and/or other wireless transfer stations can include: devices and/or other wireless transfer stations used for selected applications, devices and/or other wireless transfer stations with different voltage inputs or outputs, devices and/or other wireless transfer stations with different current inputs or outputs, and so forth. In another embodiment, the different types of devices can use different types of wireless transfer stations. In another embodiment, different station IDs for different wireless transfer stations can be associated with selected types of devices. In one example, each device and/or wireless transfer station can determine when a wireless transfer station coupled to the device is a wireless transfer station that is compatible with the device using the station ID of the wireless transfer station and/or the device ID of the device. In one embodiment, a device ID, a station ID, and/or a battery ID can include: serial number information of the device, the station, or the battery; a manufacturing date of the device, the station, or the battery; a manufacturing location of the device, the station, or the battery; and/or a version number of the device, battery, or wireless transfer station, respectively.

Figure 15:
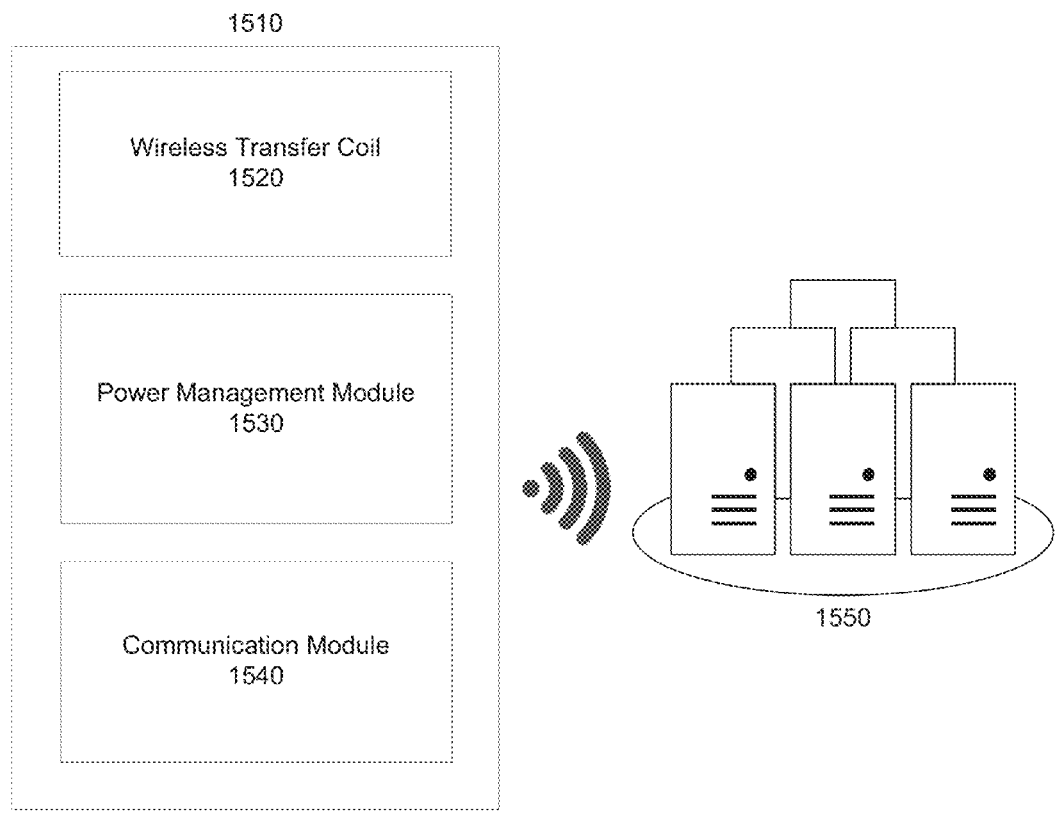
FIG. 15 depicts a wireless transfer station in accordance with an example.

FIG. 15 shows a wireless transfer station 1510 that can include: wireless transfer coil 1520, a power management module 1530, and a communications module 1540. In one embodiment, the wireless transfer station 1510 can communicate with one or more other wireless transfer stations or one or more devices using the communication module 1540. In one embodiment, the communication module 1540 of the wireless transfer station 1510 can use a communications network to communicate the data to a device and/or another wireless transfer station. In one embodiment, the wireless transfer station 1510 can use the communications module 1540 to communicate data or information. In another embodiment the data or information can include communication information, such as an Internet Protocol (IP) address of the wireless transfer station, a media access control (MAC) address of the wireless transfer station, and/or a communication link quality.

The communications module 1540 can include wireless communication capabilities and/or cellular communication capabilities. In one embodiment, the wireless transfer station 1510 can communicate using an unlicensed band in a wireless network, such as a wireless local area network (WLAN). In one embodiment, the WLAN can operate based on a standard such as the Institute of Electronics and Electrical Engineers (IEEE) 802.11-2012, IEEE 802.11ac, or IEEE 802.11ad standards. In another embodiment, the communications module 1540 can communicate using unlicensed portions of the radio spectrum, such as Bluetooth v1.0, Bluetooth v2.0, Bluetooth v3.0, Bluetooth v4.0, IEEE 802.15.4-2003 (ZigBee 2003), IEEE 802.15.4-2006 (ZigBee 2006), IEEE 802.15.4-2007 (ZigBee Pro). In another embodiment, the communications module can communicate using licensed bands in a cellular network. In one embodiment, the cellular network may be 3GPP LTE Rel. 8, 9, 10, 11, or 12 networks and/or IEEE 802.16p, 802.16n, 802.16m-2011, 802.16h-2010, 802.16j-2009, 802.16-2009.

In one embodiment, the communications module 1540 of the wireless transfer station 1510 can communicate data or information with another wireless transfer station using induction communication or a resonance communication. In one embodiment, the wireless transfer station 1510 can receive data from a first device using the induction communication or the resonance communication and relay the data to another wireless transfer station, such as a wireless transfer station attached to a wall or floor.

In one embodiment, the wireless transfer station 1510 can determine state information for a rechargeable battery, battery cell, system, subsystem, or overall state of the wireless transfer station 1510. In another embodiment, the overall state of the wireless transfer station 1510 can be a state where the wireless transfer station 1510 may be malfunctioning or not working properly. In one example, when the wireless transfer station 1510 determines that the wireless transfer station 1510 may be malfunctioning or not working properly, the wireless transfer station 1510 can indicate to a user of the wireless transfer station 1510 and/or a third party that the wireless transfer station 1510 may be malfunctioning or not working properly. In another embodiment, when the wireless transfer station determines that the wireless transfer station 1510 may be malfunctioning or not working properly, the wireless transfer station 1510 can use the communications module 1540 to communicate the state information to another wireless transfer station.

In one embodiment, the wireless transfer station 1510 can be a communication hub between multiple devices and/or wireless transfer stations. In one example, the wireless transfer station 1510 can be integrated into a medical cart. In this example, the medical cart can receive data from a first device using the communications module 1540 in a hospital room and relay the data to another wireless transfer station, such as a wireless transfer station attached to a wall or floor.

In one embodiment, when a wireless transfer station 1510 is coupled to another wireless transfer station or located adjacent to the other wireless transfer station, the wireless transfer station 1510 can communicate with the other wireless transfer station using the communications module 1540. In another embodiment, when the wireless transfer station 1510 is attached to a device or adjacent to the device, such as a wheeled medical cart, the wireless transfer station 1510 can communicate with the medical device using the communications module 1540.

In one embodiment, the wireless transfer station 1510 can monitor an energy usage of the wireless transfer station 1510 and/or another wireless transfer station and determine state information of the wireless transfer station 1510 and/or the other wireless transfer station, such as when the wireless transfer station 1510 and/or the other wireless transfer station may be malfunctioning or not working properly. In one example, when the wireless transfer station 1510 consumes energy outside of a selected range, e.g. an excessive amount of energy or an insufficient amount of energy, the wireless transfer station 1510 can determine that the state of the wireless transfer station 1510 may be a malfunctioning state or a not working properly state. In another example, when the wireless transfer station 1510 consumes energy within a selected range, e.g. a normal energy consumption level, the wireless transfer station 1510 can determine that the state of the wireless transfer station 1510 may be a working properly state.

In one embodiment, the wireless transfer station 1510 can provide the energy consumption level information to a data collection device 1550. In another embodiment, the data collection device 1550 can be a computing device, such as a central server or a data center. In another embodiment, the data collection device 1550 can be another wireless transfer station. In another embodiment, the data collection device 1550 can be integrated into the computing device and/or the other wireless transfer station. In another embodiment, the data collection device 1550 can use the energy consumption level information to determine that the wireless transfer station 1510 may be malfunctioning or not working properly. In one embodiment, the data collection device 1550 can indicate to the user of the device or a third party that the wireless transfer station 1510 may be malfunctioning or not working properly. In one embodiment, the wireless transfer station 1510 can transfer energy to one or more devices, receive energy from one or more devices or sources, and/or communicate data or information with one or more devices.

In one embodiment, the data collection device 1550 can record and/or analyze energy information and/or state information for one or more devices and/or one or more wireless transfer stations in a wireless transfer system. In another embodiment, the data collection device 1550 can analyze the energy information and/or state information to determine the overall state of the wireless transfer system. The overall state of the wireless energy system can include: which wireless transfer stations and/or devices are being used in the wireless transfer system, a battery level of each wireless transfer station and/or device in the wireless energy system, a number of wireless transfer stations and/or devices malfunctioning in the wireless energy system, and so forth. In another embodiment, the data collection device 1550 can analyze the energy information and/or state information to diagnose when one or more devices and/or one or more wireless transfer stations in the wireless transfer system are malfunctioning.

In one embodiment, the data collection device 1550 can store information from one or more devices and/or one or more wireless transfer stations. In one example, when the wireless transfer station 1510 is in communication with the data collection device 1550, the wireless transfer station 1510 can communicate information to the data collection device 1550 and the data collection device 1550 can store the information. In another embodiment, the wireless transfer station 1510 can store information (such as on a non-transitory computer-readable medium) and/or communicate the information to another wireless transfer station, such as a wireless transfer station integrated into a wheeled medical cart, when the wireless transfer station 1510 is in communication with the other wireless transfer station.

In one embodiment, the data collection device 1550 can be an information hub device. In another embodiment, the data collection device 1550 can be integrated into a mobile information hub device, such as a wheeled medical cart, and can receive information from one or more devices and/or one or more wireless transfer stations within a communications coverage range of the mobile information hub device. In another embodiment, the mobile communication hub device can communicate the information to a stationary communication hub device. In one example, the stationary communication hub device can be a communication hub device coupled to a computing device or integrated into a computing device, such as a server. In one embodiment, the server can be a third party server, e.g. a server external to an information technology (IT) infrastructure of a medical facility where the one or more devices and/or the one or more wireless transfer stations are used. In another example, the stationary communication hub device can be another wireless transfer station, such as a wireless transfer station plate or wireless transfer station floor mat.

In one embodiment, the data collection device 1550 can associate a device ID of a device to information for the device and/or a wireless transfer station coupled to the device. In another embodiment, the data collection device 1550 can associate a station ID of a wireless transfer station to information for the wireless transfer station and/or a device the wireless transfer station is coupled to. In another embodiment, the wireless transfer station can link a battery ID of one or more batteries and/or battery cells of a wireless transfer station to information for the wireless transfer station. In one example, the device ID, the station ID, and/or the battery ID can be used to track information for one or more devices and/or for one or more wireless transfer station. In another embodiment, the device ID, the station ID, and/or the battery ID can be used to determine a location of an associated wireless transfer station and/or an associated device.

In one embodiment, the data collection device 1550 can communicate with one or more devices and/or one or more wireless transfer stations to determine management information of the one or more devices and/or the one or more wireless transfer stations. The management information can include: a battery capacity level of a device of the one or more devices or a wireless transfer station of the one or more wireless transfer stations, priority level of the device or the wireless transfer station, an energy consumption rate of the device or the wireless transfer station, a number of times the device or the wireless transfer station has been charged, an estimation of a number of charges remaining for the device or the wireless transfer station, an operational temperature of the device or the wireless transfer station, an internal temperature of the device or the wireless transfer station, a device ID of the device, a battery ID of one or more batteries of the wireless transfer station, a station ID of the wireless transfer station, and so forth.

In one embodiment, the data collection device 1550 can record and/or track the management information of the one or more devices or the one or more wireless transfer stations. In one example, each of the one or more devices and/or the one or more wireless transfer stations can be assigned a device ID or station ID, respectively. In this example, data collection device 1550 can receive the management information for each of the one or more devices and each of the one or more wireless transfer station in a communications coverage area of the data collection device 1550 and associate the management information with the device ID or battery ID, respectively.

In one embodiment, the wireless transfer station 1510 can receive control information from another wireless transfer station or a computing device in the wireless transfer system. In one example, the control information can include: an estimated total battery life remaining of the other wireless transfer station or computing device, an energy usage level adjustment signal of the other wireless transfer station or computing device, a wireless transfer station recharge reminder, and so forth.

In one embodiment, the wireless transfer station 1510 can communicate data or information over a cellular network or a wireless network using a data channel and communicate control information over a cellular network or a wireless network using a control channel. For example, a wheeled medical cart with an integrated wireless transfer station can receive a computer application using a data channel of a cellular network and receive energy information for the wheeled medical cart using a control channel.

Figure 16:
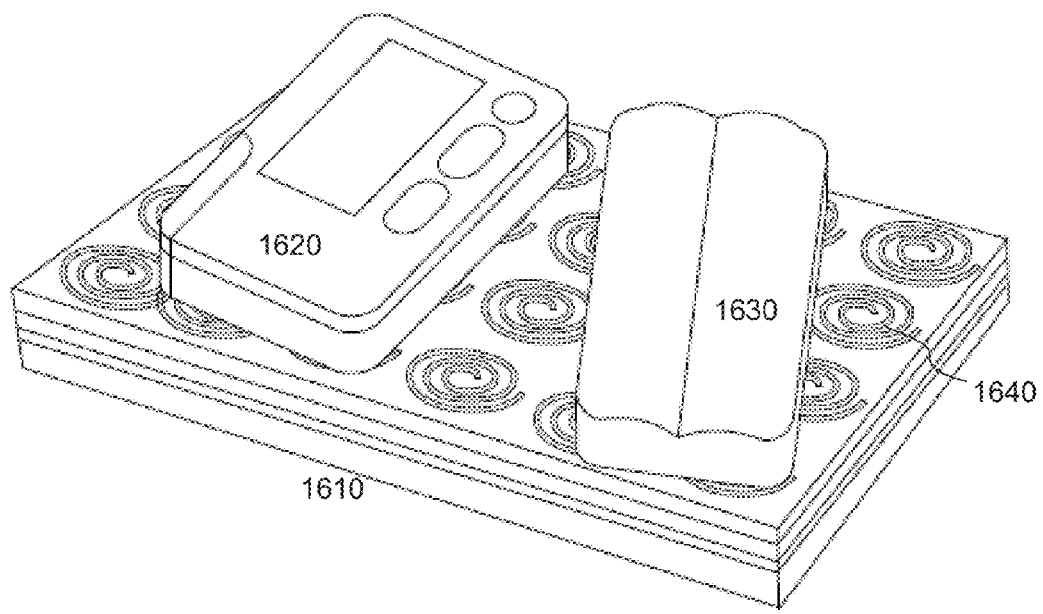
FIG. 16 depicts a wireless transfer hub transferring energy and/or information with an electronic device and/or another wireless transfer station using wireless transfer coils in accordance with an example.

In one embodiment, a wireless transfer station can be a wireless transfer hub (e.g. energy and/or data transfer) for a plurality of selected devices and/or other wireless transfer stations. FIG. 16 illustrates a wireless transfer hub 1610 transferring energy and/or information with an electronic device 1620, such as a medical device, and/or another wireless transfer station 1630 using wireless transfer coils 1640. In one embodiment, the electronic device 1620 and the other wireless transfer station 1630 can exchange energy and/or information with the wireless transfer station 1610 at the same time or at different times. In another embodiment, the electronic device 1620 and the other wireless transfer station 1630 can transfer energy and/or information with the wireless transfer hub 1610 using different wireless transfer coils 1640.

In one example, the wireless transfer hub 1610 coupled to a medical cart can wirelessly provide selected levels of energy to systems and subsystems of the medical cart and/or other devices coupled to the medical cart. In one embodiment, the wireless transfer hub 1610 coupled to the medical cart can receive energy and/or data from a wireless transfer station and relay the energy and/or data to systems and subsystems of the medical cart and/or other devices using one or more repeater coils.

In one embodiment, a medical cart or a device can have an integrated wireless transfer station to provide energy to systems and/or subsystems of the medical cart or the device when one or more external wireless transfer stations (e.g. non-integrated wireless transfer stations) are being recharged. In one embodiment, the integrated wireless transfer station can include one or more wireless transfer coils to receive energy and/or data from another wireless transfer station. In one example, the medical cart or the device can receive energy from the one or more external wireless transfer stations until an energy level of the one or more external wireless transfer stations is depleted or decreases below a threshold energy level. In this example, when the energy level of the one or more external wireless transfer stations is depleted or decreases below a threshold energy level, the medical cart or the device can be positioned adjacent a transmitter coil of another wireless transfer station and the one or more external wireless transfer stations can receive energy for recharging. In one embodiment, while the one or more external wireless transfer stations receive energy for recharging, the integrated wireless transfer station can provide energy to the medical cart or the device.

In one embodiment, the integrated wireless transfer station can receive energy from the other wireless transfer station to recharge one or more batteries of the integrated wireless transfer station. In another embodiment, the integrated wireless transfer station can receive energy from the one or more external wireless transfer stations to recharge the one or more batteries of the integrated wireless transfer station. In another embodiment, when the one or more external wireless transfer stations receive energy from another wireless transfer station, the one or more external wireless transfer stations can provide partial or full energy to the medical cart or the device.

In one embodiment, when the energy level of the one or more external wireless transfer stations is depleted or decreases below a threshold energy level, the one or more external wireless transfer stations can be removed from the medical cart or the device and placed adjacent a transmitter coil of another wireless transfer station to receive energy to recharge the external wireless transfer station. In one embodiment, while the one or more external wireless transfer stations are removed for recharging and/or until one or more other external wireless transfer stations are attached to the medical cart or the device, the integrated wireless transfer station can provide energy to one or more system or subsystem of the medical cart or the device. In one embodiment, when the medical cart or the device is placed adjacent to a transmitter coil of a wireless transfer station, the integrated wireless transfer station can receive energy from the wireless transfer station to recharge the integrated wireless transfer station.

In one embodiment, the medical cart or a device can include a wireless transfer coil to transfer energy and/or data with another wireless transfer station. In one example, the medical cart or a device can use the wireless transfer coil to receive energy and provide energy directly to one or more systems and/or subsystems of the medical cart or the device and/or provide energy to an energy source, such as a battery, of the medical cart or the device. In one example, the medical cart or the device with the wireless transfer coil can be placed near a transmitter coil of a wireless transfer station and the wireless transfer coil can relay energy to one or more systems and/or subsystems of the medical cart or the device.

Figure 17:
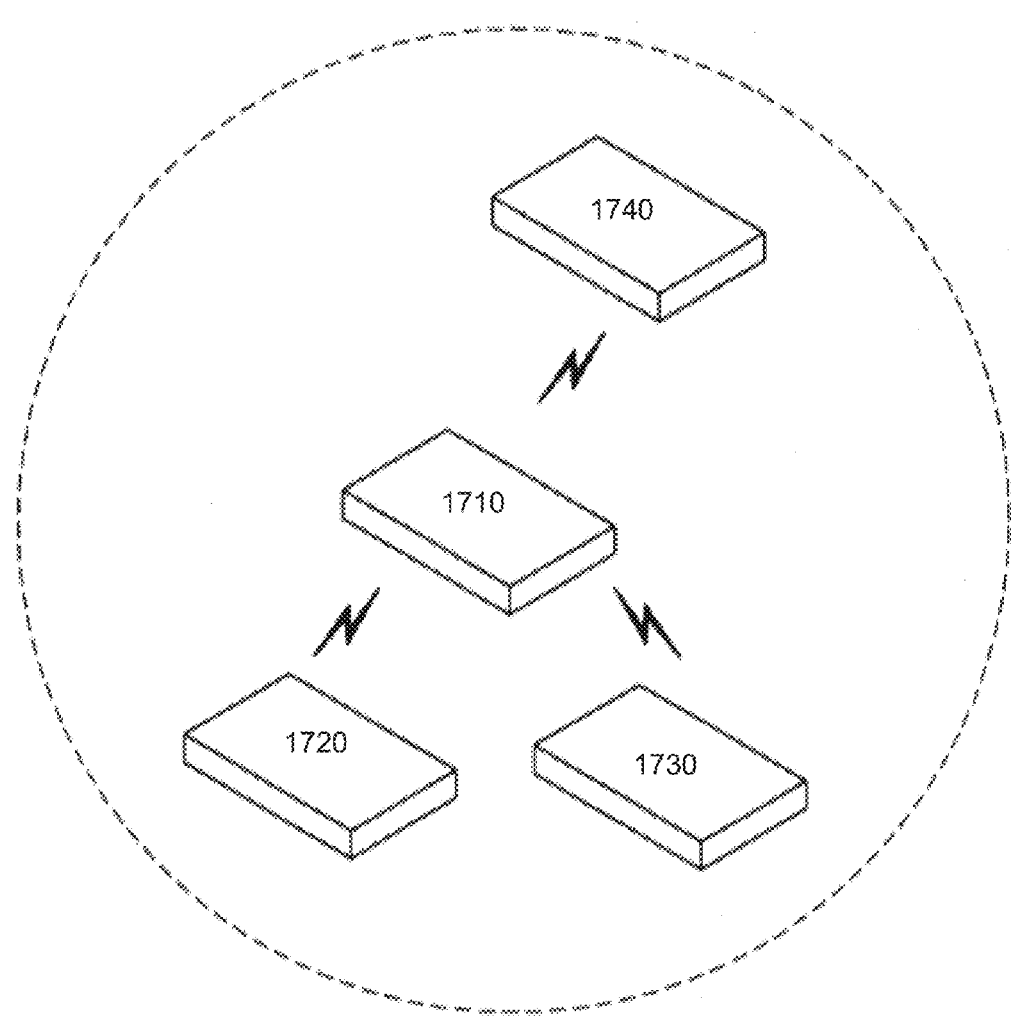
FIG. 17 depicts a wireless transfer station configured to communicate with other wireless transfer stations in accordance with an example.

FIG. 17 shows a wireless transfer station 1710 configured to communicate with other wireless transfer stations 1720, 1730, and/or 1740 and determine which of the one or more other wireless transfer stations 1720, 1730, and/or 1740 is capable and/or available to provide energy to a selected device and/or a selected wireless transfer station. In one example, the selected device or the selected wireless transfer station can send a wireless transfer request to the wireless transfer station. When the wireless transfer station 1710 is not compatible with the selected device or the wireless transfer station 1710 is not available to provide energy to the selected device, the wireless transfer station 1710 can communicate with the one or more other wireless transfer stations 1720, 1730, and/or 1740 to locate an available wireless transfer station of the one or more other wireless transfer stations 1720, 1730, and/or 1740 for the selected device or the selected wireless transfer station to receive wireless energy. When the wireless transfer station 1710 determines that available wireless transfer station can provide energy to the selected device or the selected wireless transfer station, the wireless transfer station 1710 can provide the selected device or the selected wireless transfer station with transfer station information for the available wireless transfer station.

In one embodiment, the transfer station information can include: directions to one of the other wireless transfer stations 1720, 1730, or 1740; authentication information to receive energy from the other wireless transfer stations 1720, 1730, or 1740; a number of available wireless transfer coils at the other wireless transfer stations 1720, 1730, or 1740; a type of wireless transfer coils available at the other wireless transfer stations 1720, 1730, or 1740; an energy capabilities of the other wireless transfer stations 1720, 1730, or 1740; and so forth. In one embodiment, when more than one of the other wireless transfer stations 1720, 1730, or 1740 are available to provide energy to the selected wireless transfer station or the selected device, the selected wireless transfer station or the selected device can select which one of the one or more other wireless transfer stations 1720, 1730, or 1740 to receive energy from based on charging criteria. The charging criteria can include: an energy output capability of each of the one or more available other wireless transfer stations 1720, 1730, or 1740; a location of each of the one or more available other wireless transfer stations 1720, 1730, or 1740; a distance from the selected device or the selected wireless transfer station to each of the one or more available other wireless transfer stations 1720, 1730, or 1740; a number of other devices or other wireless transfer stations receiving energy from each of the one or more available other wireless transfer stations 1720, 1730, or 1740, and so forth.

In one example, the wireless transfer station 1710 is not compatible with the selected device or the selected wireless transfer station when a wireless transfer coil of the selected device or wireless transfer coils of the selected wireless transfer station are a different shape or size than a wireless transfer coil of the wireless transfer station 1710. In another example, the wireless transfer station 1710 is not compatible with the selected device or the selected wireless transfer station when a wireless transfer coil of the selected device or a wireless transfer coil of the selected wireless transfer station receives data and/or wireless energy at a different resonant frequency range than a resonant frequency range of a wireless transfer coil of the wireless transfer station 1710.

Figure 18:
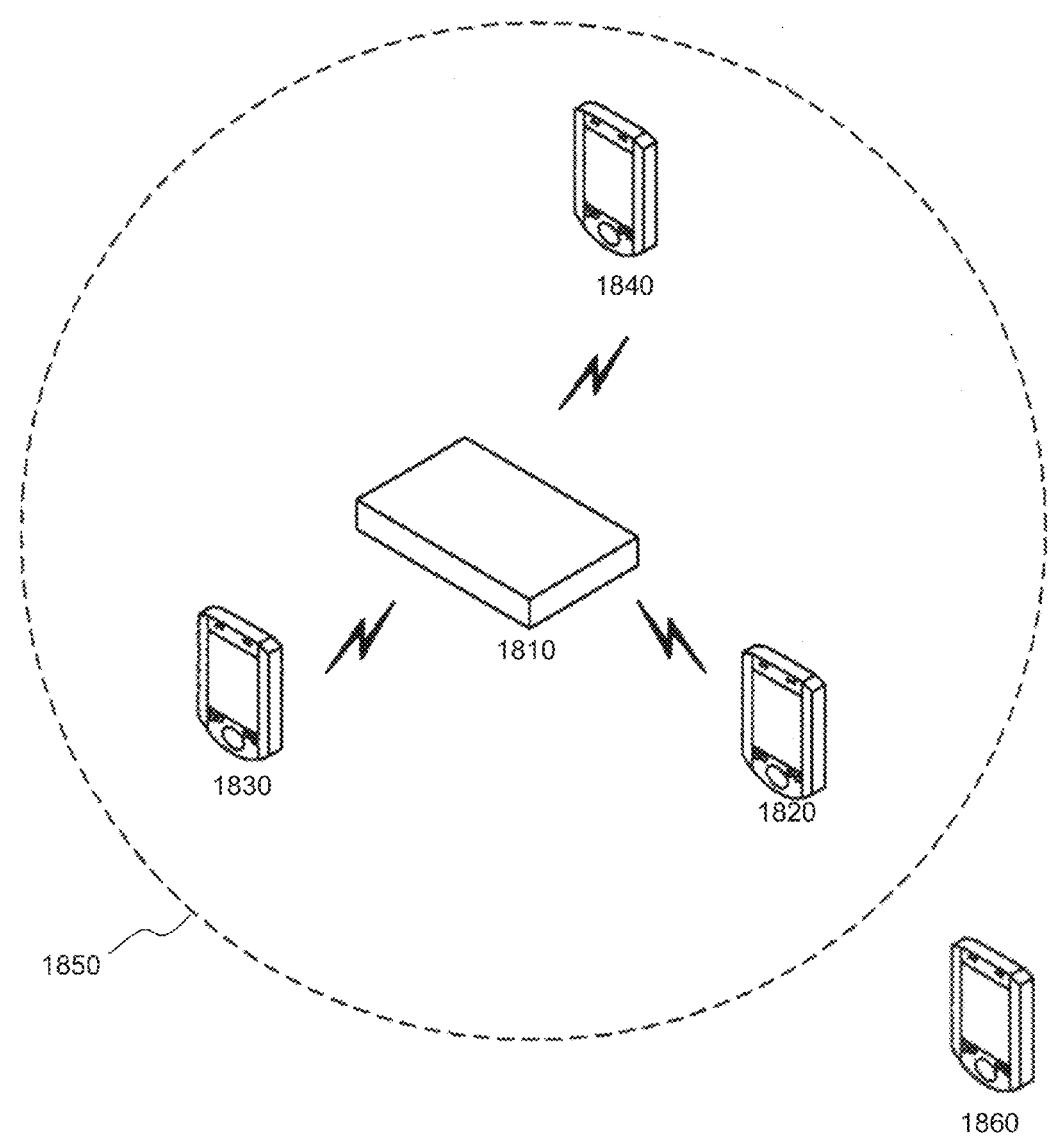
FIG. 18 depicts a wireless transfer station transferring energy and/or data with one or more wireless transfer stations and/or devices within a selected range in accordance with an example.

FIG. 18 shows a wireless transfer station 1810 transferring energy and/or data with one or more wireless transfer stations and/or devices 1820, 1830, and 1840 within a selected range 1850. In one embodiment, the wireless transfer station 1810 can adjust the selected range 1850 based on selected criteria, such as a number of wireless transfer stations and/or devices within a threshold range of the wireless transfer station 1810, a number of devices or other wireless transfer stations the wireless transfer station 1810 can support transferring energy and/or data to, and so forth. In one example, the wireless transfer station 1810 can transfer energy and/or data with wireless transfer stations and/or devices 1820, 1830, and 1840 that are within the selected range 1850 and not transfer energy and/or data with wireless transfer station and/or device 1860.

In one embodiment, a device and/or a wireless transfer station can store data or information, such as on a non-transitory computer-readable medium coupled to the device or the wireless transfer station. In another embodiment, the wireless transfer station can be a communication hub to receive and/or store data or information from a device and/or other wireless transfer station. In one example, the device and/or the other wireless transfer station can monitor selected events and communicate selected event information to a wireless transfer station coupled to the device or the communication hub. In one embodiment, the selected event information can include safety information, such as: over current information, over voltage information, under current information, under voltage information, short circuit information, cell imbalance information, over temperature information, communication error information, energy usage information, a change in temperature information, a change in temperature versus time ration, voltage information of one or more batteries and/or one or more battery cells of the wireless transfer station, and so forth. In one embodiment, the wireless transfer station can include a plurality of battery cells, such as a 15-cell battery with 5 cells in a series and 3 cells in parallel. In one example, the safety information can include voltage information of each cell or a difference between voltages of each cell. In one embodiment the voltage information of each cell or the difference between voltages of each cell can be used to determine a balance of each cell of the battery and/or an approximate age of the battery or the cell. In one embodiment the selected event information can be an inserted indicator indicating when a wireless transfer station has been coupled to a device or wireless transfer station.

In another embodiment the selected event information can be error information. In one example, the error information can include: fuse information, such as blown fuse information; a battery cell status, such as a failed cell of a battery of the wireless transfer station; a wire connectivity status, such as a wire break in the wireless transfer station; an over temperature event, such as when an internal temperature of the wireless transfer station exceeds 75 degrees Celsius; an over or under voltage and/or current event, such as when a voltage or current level of the wireless transfer station exceeds a selected threshold; a run time of the wireless transfer station, such as an actual runtime of the wireless transfer station versus a designed run time of the wireless transfer station; an outside of warranty indication; and firmware and/or software error codes. In one embodiment, error information can be determined based on an actual full capacity level of a battery of the wireless transfer station compared to a designed capacity level of the battery. In one example, when the actual full capacity level of the battery is 20 amp hours and the design capacity level is 30 amp hours, the difference in actual versus design capacity level (10 amp hours) can indicate an error of the wireless transfer station. In another embodiment, the wireless transfer station and/or device can use the safety information and/or the error information to determine when the wireless transfer station has been used outside of warranted uses, e.g. wireless transfer station abuse.

In one embodiment, when the device and/or the wireless transfer station detects a safety event and/or an error event, the device and/or the wireless transfer station can cease transferring wireless energy. In one example, the wireless transfer station can cease transferring wireless energy when: a full charge capacity is below a selected threshold; a current transfer level and/or voltage transfer level is outside a selected threshold; a current usage level and/or voltage usage level is outside a selected threshold; a wireless transfer station is not receiving information from a module, system, subsystem, battery, and/or battery cell of the wireless transfer station; an other wireless transfer station is not receiving energy or data from the wireless transfer station or the device; the device and/or the wireless transfer station are not operating using a most recent version of an operation system (OS) of the device and/or the wireless transfer station; and/or an internal temperature of the wireless transfer station, a battery or battery cell of the wireless transfer station, and/or the device rise beyond a threshold level.

In one embodiment, the device and/or the wireless transfer station can measure, store, and/or communicate an amount of time a selected event may occur. In one example, the device and/or the wireless transfer station can measure, store, and/or communicate an amount of time an over temperature event occurs. In another embodiment, the device and/or the wireless transfer station can measure, store, and/or communicate selected event information at selected periods of time, such as at periodic intervals (e.g. every hour, twice a day, etc.). In another embodiment, when the device and/or the wireless transfer station detect a selected event, such as a selected safety event, the device and/or the wireless transfer station can adjust the selected period of time for measuring and/or storing selected event information. In one example, when an error or safety event occurs the device and/or the wireless transfer station can adjust the selected period of time for measuring and/or storing selected event information from once an hour to once a minute. One advantage of adjusting the selected period of time for measuring and/or storing selected event information can be to conserve battery energy and/or storage space when a selected event has not occurred and to capture a finer degree of information detail during the time period that the selected event occurs.

In one embodiment, the wireless transfer station and/or the device can send a heartbeat signal to another wireless transfer station and/or another device to indicate where the wireless transfer station and/or the device is located. In one example the wireless transfer station and/or the device can send out a heartbeat signal every 24 hours to indicate a location of the wireless transfer station and/or the device. In another embodiment, the wireless transfer station and/or device can include a radio frequency identification (RFID) tag or RFID transmitter to indicate a location of the wireless transfer station and/or device. In one example, to locate the wireless transfer station and/or device when the wireless transfer station and/or device has lost all energy or power, a user can use an RFID reader or RFID scanner to determine a location of the wireless transfer station and/or the device.

In one embodiment, the device and/or the wireless transfer station can include a real-time clock to measure time. In another embodiment, the device and/or the wireless transfer station can include a timer to measure time, where the timer begins at a selected point in time, such as a manufacture day and time.

In one embodiment, a wireless transfer station coupled to a device can receive data or information from the device and store the received data or information. In another embodiment, a wireless transfer station can be coupled to another wireless transfer station and when the coupled wireless transfer station receives energy from the other wireless transfer station, the coupled wireless transfer station can communicate stored information to a data collection device, such as a data collection device integrated into the other wireless transfer station. In one example, a device can communicate information stored on the device via the wireless transfer station to the other wireless transfer station. In another example, the device can communicate the stored information directly to the other wireless transfer station.

In one embodiment, the wireless transfer station can use a communications module (as shown in FIG. 4) to communicate selected received data and/or selected stored data to a third-party device. In one embodiment, the wireless transfer station can communicate the selected information to a third-party device. In another embodiment, the third-party device can be a server external to a medical facility where the wireless transfer station is located, a cloud-based information system, or another computing device external to the medical facility where the wireless transfer station is located.

In another embodiment, the wireless transfer station and/or the third-party device can receive selected information for a plurality of wireless transfer stations. In another embodiment, the wireless transfer station and/or the third-party device can aggregate the selected information received from the plurality of wireless transfer stations and/or devices. In another embodiment, the devices can be non-wireless energy devices (e.g. devices without wireless transfer coils) with communications modules. In another embodiment, the devices can be wireless energy devices (e.g. devices with wireless transfer coils). In another embodiment, the wireless transfer station and/or the third-party device can analyze the aggregated selected information to determine selected result information.

In another embodiment, the wireless transfer station and/or the third-party device can format the aggregated selected information to be compatible with a computing device, such as a server, of the medical facility. In another embodiment, the wireless transfer station and/or the third-party device can filter the aggregated selected information to exclude selected information and/or included selected information of the aggregated selected information. In another embodiment, the wireless transfer station and/or the third-party device can format the aggregated selected information to a format compatible with a computing device or a computing system, such as a server system, that is part of an internal computing system or internal network system of a facility where the devices and/or the wireless transfer stations are located. In another embodiment, the wireless transfer station and/or the third-party device can communicate the formatted information to the internal computing device or the internal computing system. In another embodiment, the third-party device can be a device external to the internal computing system or internal network system. In another embodiment, the third-party device can receive information from one or more devices or one or more wireless transfer stations, aggregate and/or format the received information, and communicate the aggregated information to the internal computing device or the internal computing system.

One advantage of communicating the formatted information from the third-party device to the internal server system is that the internal server system can receive the formatted information in a bundle or package. In one example, a medical facility, such as hospital, may have strict regulatory procedures for accessing a server at the medical facility. The regulatory procedures may prohibit or limit the access of a device and/or of a wireless transfer station to the medical facility network or server. In this example, a third-party server sending the aggregated information to the medical facility server can limit a number of devices accessing the medical facility network or server and/or provide a more secure communication channel to communicate the information to the medical facility network or server.

Figure 19:
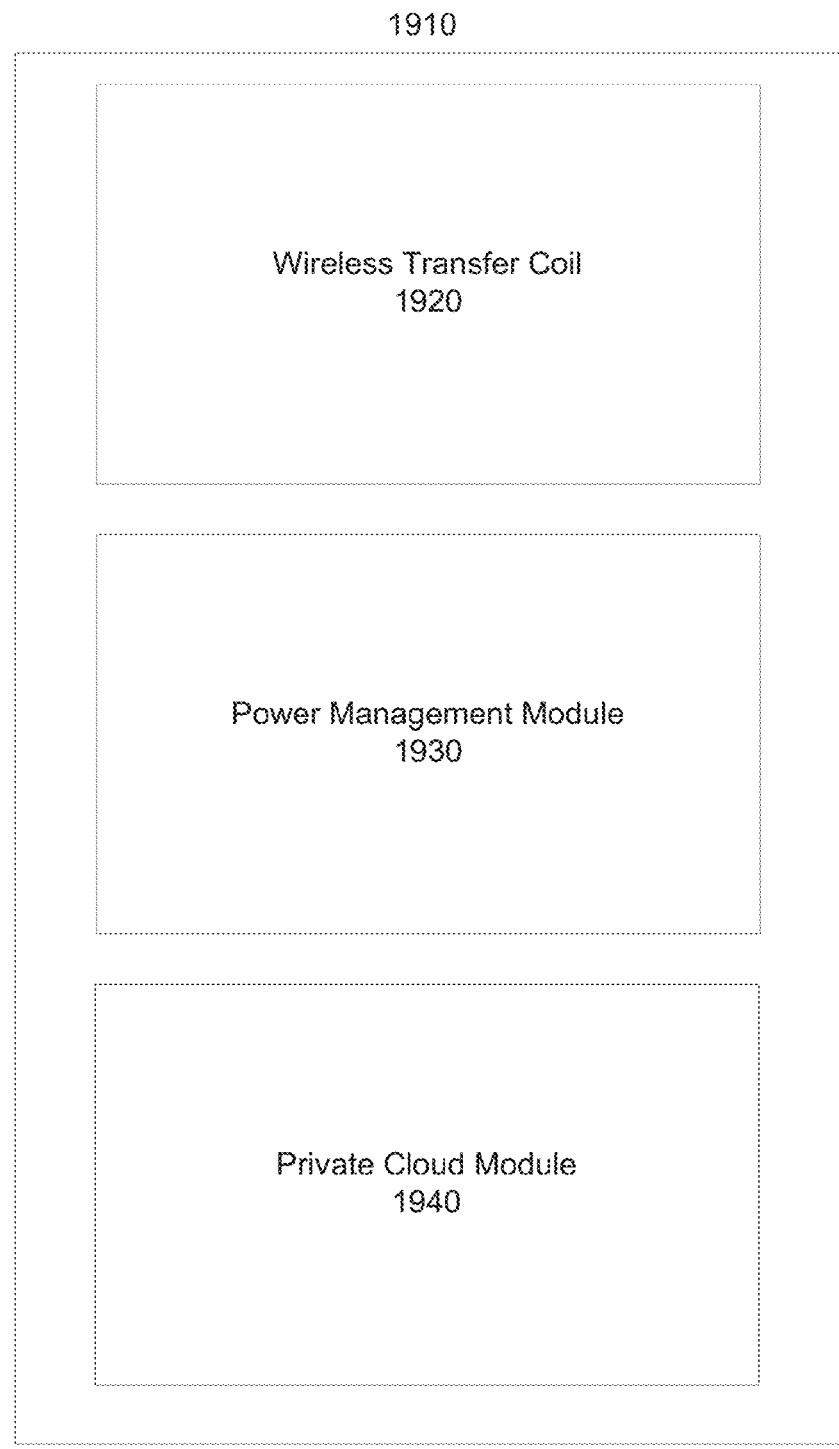
FIG. 19 depicts a wireless transfer station in accordance with an example.

FIG. 19 illustrates a wireless transfer station 1910. FIG. 19 further illustrates that the wireless transfer station 1910 can include a wireless transfer coil 1920, a power management module 1930, and a private cloud module 1940. In one example, the power management module 1930 can convert energy received from an energy source, such as another wireless transfer station or an alternating current (AC) energy outlet, to a selected amperage level, a selected current level, a selected voltage level, and/or a selected wattage level. In another embodiment, the wireless transfer station 1910 can include one or more batteries, such as rechargeable batteries. In one embodiment, the wireless transfer coil 1920 can be a transmitting coil and/or a receiving coil.

In one embodiment, the private cloud module 1940 can create a private cloud server that can be used to communicate data between devices and/or other wireless transfer stations. One advantage of using the private cloud server of the private cloud module 1940 is that the private cloud server does not interfere with the throughput of other standard communication systems such as a cellular network, a wireless network, or a communications network of a facility where the wireless transfer station is located.

Figure 20:
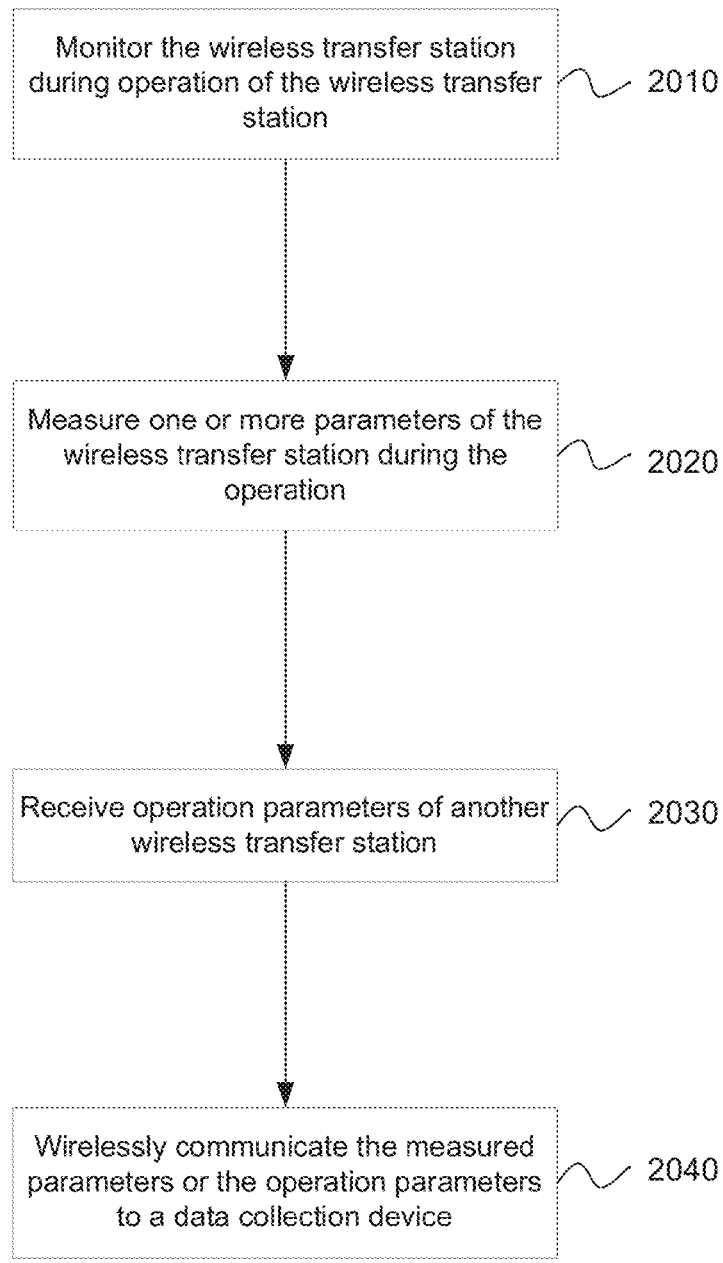
FIG. 20 depicts the functionality of computer circuitry of an asset management module operable to communicate energy management information for a wireless transfer station in accordance with an example.

FIG. 20 uses a flow chart 2000 to illustrate the functionality of one embodiment of the computer circuitry with an asset management module operable to communicate energy management information for a wireless transfer station. The functionality may be implemented as a method or the functionality may be executed as instructions on a machine, where the instructions are included on at least one computer readable medium or one non-transitory machine readable storage medium. In one embodiment, the asset management module can be configured to monitor the wireless transfer station during operation of the wireless transfer station, as in block 2010. In another embodiment, the asset management module can be further configured to measure one or more parameters of the wireless transfer station during the operation, as in block 2020. In another embodiment, the asset management module can be further configured to receive operation parameters of another wireless transfer station, as in block 2030. In another embodiment, the asset management module can be further configured to wirelessly communicate the measured parameters or the operation parameters to a data collection device, as in block 2040.

In one embodiment, the data collection device can be coupled to a wireless transfer station. In another embodiment, the asset management module can be configured to associate the measured parameters with a wireless transfer station identification (ID) of the wireless transfer station. In another embodiment, the asset management module can be configured to associate the measured parameters with a device identification (ID) of the wireless transfer station. In another embodiment, the measured parameters or the operation parameters includes: a operational temperature or internal temperature of the wireless transfer station or a device coupled to the wireless transfer station; a cell balance of one or more battery cells of the wireless transfer station or the device coupled to the wireless transfer station, such as a current level of each battery cell of a voltage level of each battery cell; a cell charge status of one or more battery cells of the wireless transfer station or the device coupled to the wireless transfer station, such as a voltage capacity level, a current capacity level, or a charge rate; a cell capacity status of one or more battery cells of the wireless transfer station or the device coupled to the wireless transfer station, such as an amount of energy (e.g. amp hours) the one or more battery cells can hold; a current draw or voltage draw of the wireless transfer station or the device coupled to the wireless transfer station; a location of the wireless transfer station or the device coupled to the wireless transfer station; a charge state of the wireless transfer station or the device coupled to the wireless transfer station, such as a full, a charge level percentage, or depleted; an estimated amount of time remaining to charge the wireless transfer station or the device coupled to the wireless transfer station; an amount of time taken to previously charge the wireless transfer station or the device coupled to the wireless transfer station; a wireless power transfer efficiency of the wireless transfer station or the device coupled to the wireless transfer station; communications parameters for the wireless transfer station or the device coupled to the wireless transfer station, such as a communication bandwidth level or communications channel of the wireless transfer station or the device coupled to the wireless transfer station; a usage level of the wireless transfer station or the device coupled to the wireless transfer station; software management information of the wireless transfer station or the device coupled to the wireless transfer station, such as an operating system version, which software applications are stored on the wireless transfer station or the device coupled to the wireless transfer station, an amount of use of one or more the stored software applications, and so forth; an operational status of the wireless transfer station or the device coupled to the wireless transfer station (as discussed in the proceeding paragraphs); communication coordination information, such as when one or more of the wireless transfer station or the device coupled to the wireless transfer station can communicate information; patient data measured using device coupled to the wireless transfer station; and so forth.

In one embodiment, the asset management module can be configured to: receive operation parameters from the other wireless transfer station; aggregate the operation parameters of the other wireless transfer station with the measured parameters of the wireless transfer station; and communicate the aggregated parameters to the data collection device. In another embodiment, the measured parameters information can include: a charge level of the wireless transfer station; an amount of energy provided by the wireless transfer station to the other wireless transfer station; a number of times the wireless transfer station has received energy from the other wireless transfer station; or a type of device coupled to the wireless transfer station.

In one embodiment, the operation parameters information can include: a charge level of the other wireless transfer station; an amount of energy received by the other wireless transfer station from the wireless transfer station; a number of times the other wireless transfer station has received energy from the other wireless transfer station; or a type of device coupled to the other wireless transfer station. In another embodiment, the asset management module can be configured to: analyze the measured parameters or operation parameters; determine a system status of the wireless transfer station or the other wireless transfer station; and communicate the system status to the data collection device. In another embodiment, the system status can include an operational status of the wireless transfer station or the other wireless transfer station or an approximated usage life of the wireless transfer station or the other wireless transfer station.

In one embodiment, the asset management module can be configured to store the measured parameters or the operation parameters on a non-tangible computer readable medium coupled to the asset management module or the wireless transfer station. In another embodiment, the asset management module can be configured to communicate the stored measured parameters or operation parameters to the other wireless transfer station when the wireless transfer station receives wireless energy. In another embodiment, the asset management module can be configured to send control parameters to the wireless transfer station or the other wireless transfer station based on the measured parameters or the operation parameters.

Figure 21:
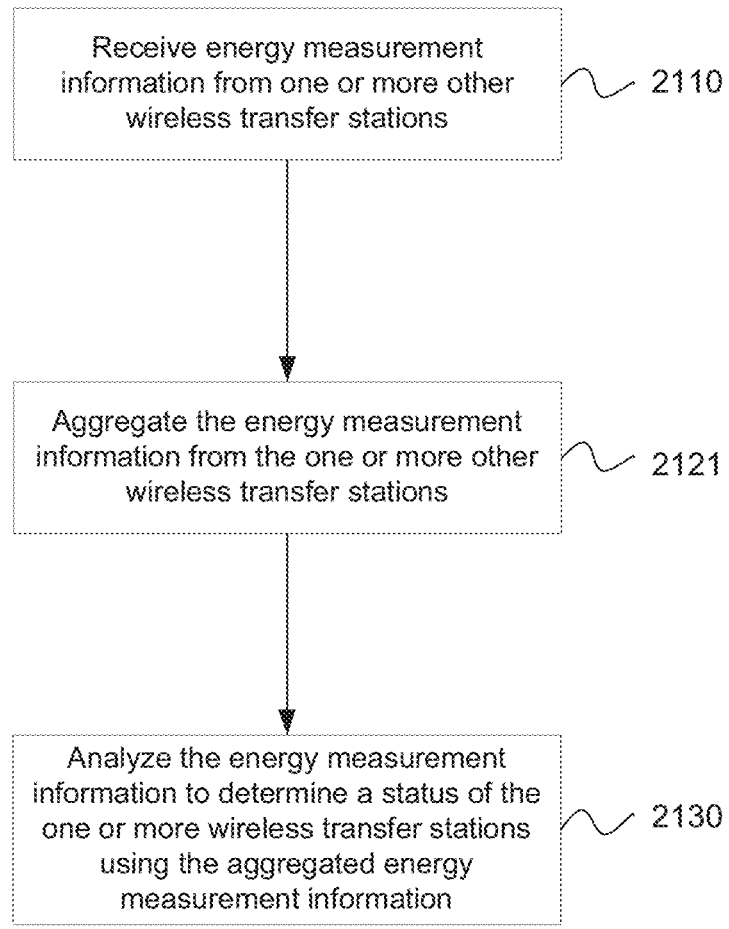
FIG. 21 depicts the functionality of computer circuitry of a wireless transfer station operable to communicate management information in accordance with an example.

FIG. 21 uses a flow chart 2100 to illustrate the functionality of one embodiment of the computer circuitry with a wireless transfer station operable to communicate management information. The functionality may be implemented as a method or the functionality may be executed as instructions on a machine, where the instructions are included on at least one computer readable medium or one non-transitory machine readable storage medium. In one embodiment, the wireless transfer station can be configured to receive measurement information from one or more other wireless transfer stations, as in block 2110. In another embodiment, the wireless transfer station can be configured to aggregate the measurement information from the one or more other wireless transfer stations, as in block 2120. In another embodiment, the wireless transfer station can be configured to analyze the measurement information to determine a status of the one or more wireless transfer stations using the aggregated measurement information, as in block 2130.

In one embodiment, the wireless transfer station can be further configured to provide energy to at least one of the one or more other wireless transfer stations and receive the measurement information from at least one of the one or more other wireless transfer stations when the wireless transfer station provides energy to the at least one of the one or more other wireless transfer stations. In another embodiment, the wireless transfer station can be further configured to send a measurement information request to at least one of the one or more other wireless transfer stations to request selected data of the measurement information of the other wireless transfer station and receive the selected data of the measurement information of the other wireless transfer station. In another embodiment, the one or more other wireless transfer stations is attached to a device or a wireless transfer station. In another embodiment, the status includes: an operational status of one of the one or more other wireless transfer stations, such as a functioning status, a malfunctioning status, a partially operational status, a non-operational status, an out of commission status, a needs repair status, a non-critical error status, a critical error status, a send a technician status, a needs replacement status, an operating system version status, and so forth; an operational status of all of the one or more other wireless transfer stations, such as an all wireless transfer stations are working properly status, an all wireless transfer stations for selected uses are functioning status, a system wide error status, a communications network working properly status, a communications network not working properly status, a status of which of the one or more other wireless transfer stations are operating on an outdated operating system or software version, and so forth; an operational status of a network of wireless transfer stations, such as a status of a bandwidth of the communications network, a status of a number of wireless transfer stations using the network, and so forth.

In one embodiment, the wireless transfer station can be further configured to communicate to a server the measurement information of the one or more wireless transfer stations, the aggregate measurement information, or the system status information of the one or more wireless transfer stations. In another embodiment, the wireless transfer station can be further configured to communicate with the one or more wireless transfer stations to determine when at least one of the one or more wireless transfer stations is available to provide energy to another of the one or more wireless transfer stations. In another embodiment, the wireless transfer station can be further configured to: receive a wireless transfer station location request for a selected wireless transfer station; identify when the selected wireless transfer station is coupled to the wireless transfer station; and report a location of the selected wireless transfer station when the selected wireless transfer station is coupled to the wireless transfer station. In another embodiment, the wireless transfer station can be further configured to enter an energy saving mode when the wireless transfer station is not providing energy to at least one of the other wireless transfer stations or communicating with one at least one of the other wireless transfer stations or a server.

Figure 22:
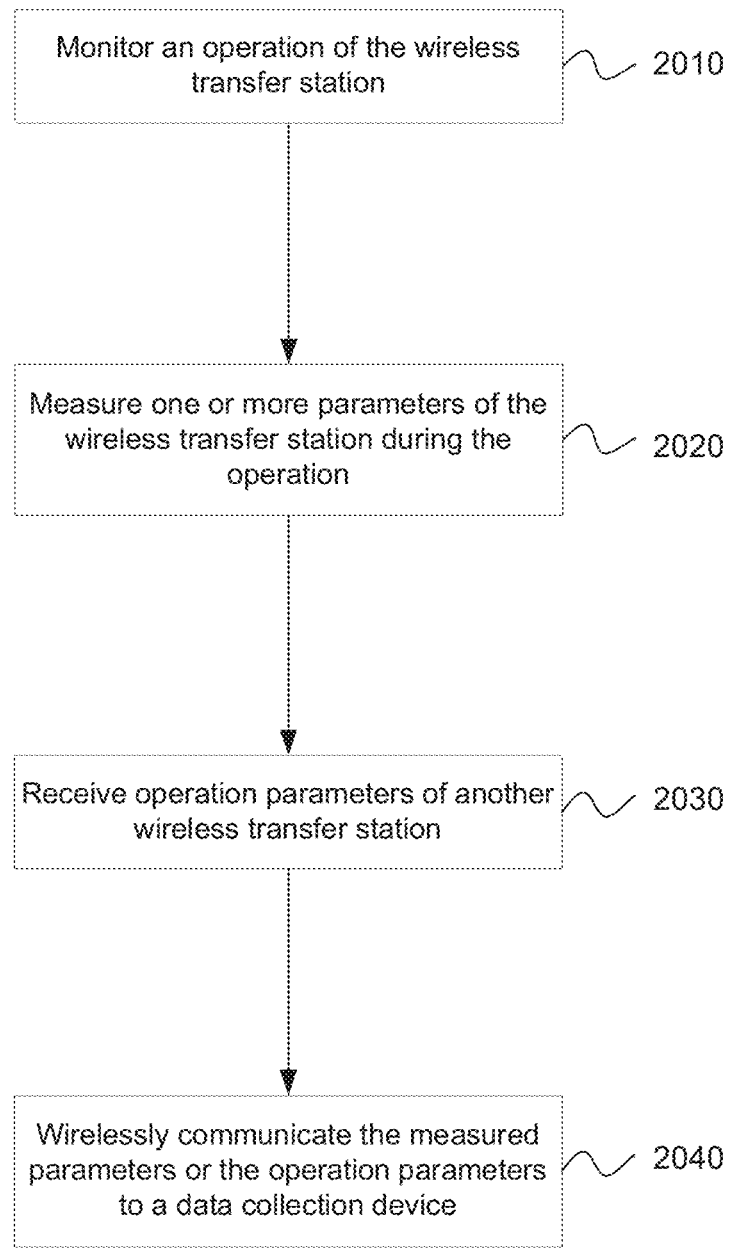
FIG. 22 depicts the functionality of computer circuitry of a wireless transfer station operable to communicate management information in accordance with an example.

FIG. 22 uses a flow chart 2200 to illustrate the functionality of one embodiment of the computer circuitry with a wireless transfer station operable to communicate management information. The functionality may be implemented as a method or the functionality may be executed as instructions on a machine, where the instructions are included on at least one computer readable medium or one non-transitory machine readable storage medium. In one embodiment, the wireless transfer station can be configured to monitor an operation of the wireless transfer station, as in block 2210. In another embodiment, the wireless transfer station can be configured to measure one or more parameters of the wireless transfer station during the operation, as in block 2220. In another embodiment, the wireless transfer station can be configured to receive operation parameters of another wireless transfer station, as in block 2230. In another embodiment, the wireless transfer station can be configured to wirelessly communicate the measured parameters or the operation parameters to a data collection device, as in block 2240.

In one embodiment, the wireless transfer station can be further configured to: provide wireless energy to a plurality of selected wireless transfer stations at different selected times; receive wireless transfer stations measurement information from the plurality of selected wireless transfer stations; associate a wireless transfer station identification (ID) with the wireless transfer station measurement information of each of the plurality of selected wireless transfer stations; aggregate the wireless transfer station measurement information of each of the plurality of selected wireless transfer stations; and communicate the aggregated wireless transfer station measurement information to the data collection device.

Figure 23:
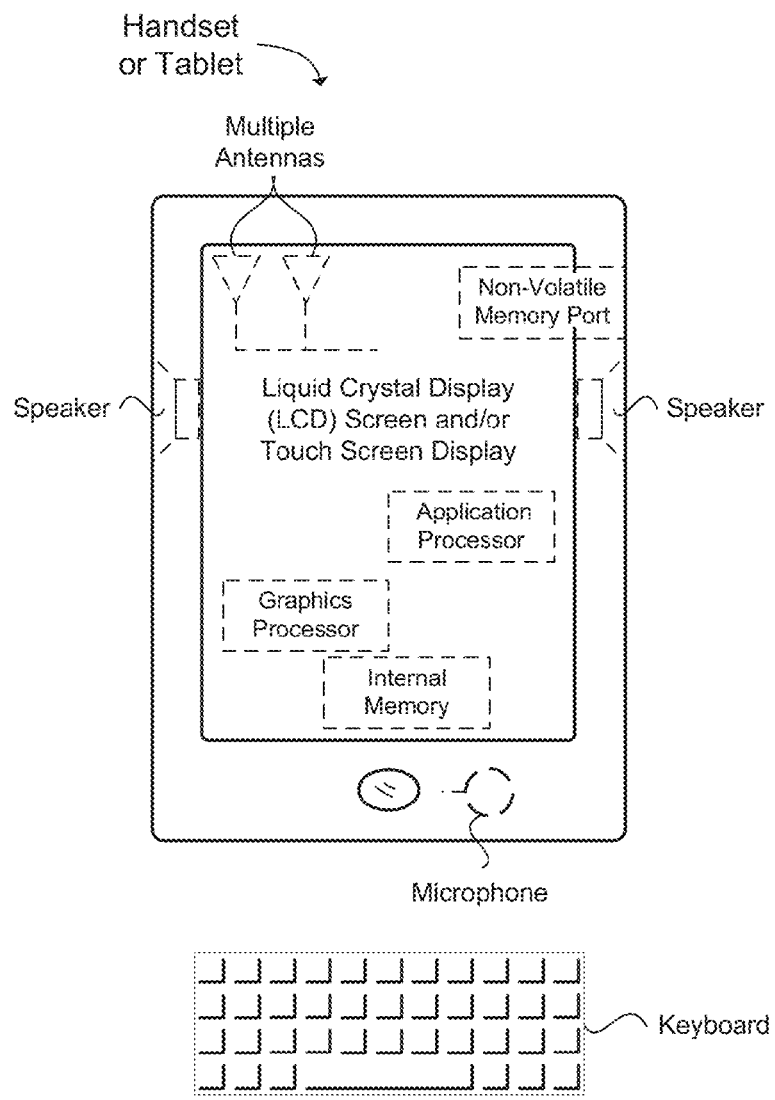
FIG. 23 illustrates a diagram of a device in accordance with an example.

FIG. 23 provides an example illustration of the device, such as a user equipment (UE), a mobile wireless device, a mobile communication device, a tablet, a handset, or other type of wireless device. The wireless device can include one or more antennas configured to communicate with a wireless transfer station. The device can be configured to communicate using at least one wireless communication standard including 3GPP LTE, WiMAX, High Speed Packet Access (HSPA), Bluetooth, and Wi-Fi. The device can communicate using separate antennas for each wireless communication standard or shared antennas for multiple wireless communication standards. The device can communicate in a wireless local area network (WLAN), a wireless personal area network (WPAN), and/or a wireless wide area network (WWAN).

FIG. 23 also provides an illustration of a microphone and one or more speakers that can be used for audio input and output from the device. The display screen can be a liquid crystal display (LCD) screen, or other type of display screen such as an organic light emitting diode (OLED) display. The display screen can be configured as a touch screen. The touch screen can use capacitive, resistive, or another type of touch screen technology. An application processor and a graphics processor can be coupled to internal memory to provide processing and display capabilities. A non-volatile memory port can also be used to provide data input/output options to a user. The non-volatile memory port can also be used to expand the memory capabilities of the device. A keyboard can be integrated with the device or wirelessly connected to the wireless device to provide additional user input. A virtual keyboard can also be provided using the touch screen.

Various techniques, or certain aspects or portions thereof, can take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a RAM, EPROM, flash drive, optical drive, magnetic hard drive, or other medium for storing electronic data. The base station and mobile station can also include a transceiver module, a counter module, a processing module, and/or a clock module or timer module. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations.

It should be understood that many of the functional units described in this specification have been labeled as modules, in order to more particularly emphasize their implementation independence. For example, a module can be implemented as a hardware circuit comprising custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like.

Modules can also be implemented in software for execution by various types of processors. An identified module of executable code can, for instance, comprise one or more physical or logical blocks of computer instructions, which can, for instance, be organized as an object, procedure, or function. Nevertheless, the executables of an identified module need not be physically located together, but can comprise disparate instructions stored in different locations which, when joined logically together, comprise the module and achieve the stated purpose for the module.

Indeed, a module of executable code can be a single instruction, or many instructions, and can even be distributed over several different code segments, among different programs, and across several memory devices. Similarly, operational data can be identified and illustrated herein within modules, and can be embodied in any suitable form and organized within any suitable type of data structure. The operational data can be collected as a single data set, or can be distributed over different locations including over different storage devices, and can exist, at least partially, merely as electronic signals on a system or network. The modules can be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention can be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics can be combined in any suitable manner in one or more embodiments. In the following description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A wireless transfer station integrated into a plate mounted on a wall operable to communicate management information, the wireless transfer station configured to:
send an energy measurement information request to a plurality of other wireless transfer stations to request energy measurement information of the plurality of other wireless transfer stations, the energy measurement information request including a request for a charge level, an estimated battery life, and an operational status;

provide energy to at least one of the plurality of other wireless transfer stations;

receive the energy measurement information, including a charge level, an estimated battery life, and an operational status, from the plurality of other wireless transfer stations when the wireless transfer station provides energy to the at least one of the plurality of other wireless transfer stations;

aggregate the energy measurement information from the plurality of other wireless transfer stations;

analyze the energy measurement information from the plurality of other wireless transfer stations to determine a system operational status of all of the plurality of other wireless transfer stations, wherein the system operational status includes at least one of the following: an all wireless transfer stations are working properly status, an all wireless transfer stations for selected uses are functioning status, a system wide error status, a communications network working properly status, or a communications network not working properly status; and communicate the aggregated energy measurement information and the system operational status to a server.

2. The wireless transfer station of claim 1, wherein the operational status includes at least one of the following:
a functioning status, a malfunctioning status, a partially operational status, a non-operational status, an out of commission status, a needs repair status, a non-critical error status, a critical error status, a send a technician status, or a needs replacement status.

3. The wireless transfer station of claim 1, further configured to communicate with the plurality of other wireless transfer stations to determine when at least one of the plurality of other wireless transfer stations is available to provide energy to another of the plurality of other wireless transfer stations.

4. The wireless transfer station of claim 1, further configured to enter an energy saving mode when the wireless transfer station is not providing energy to at least one of the plurality of other wireless transfer stations or communicating with at least one of the plurality of other wireless transfer stations or the server.

* * * * *